(12) United States Patent
Kotala et al.

(10) Patent No.: US 10,774,104 B2
(45) Date of Patent: Sep. 15, 2020

(54) DIASTEREOSELECTIVE SYNTHESIS OF PHOSPHATE DERIVATIVES

(71) Applicants: NuCana plc, Edinburgh (GB); Laurus Labs Private Ltd, Telangana (IN)

(72) Inventors: Mani Bushan Kotala, Telangana (IN); Venkata Lakshmi Narasimha Rao Dammalapati, Telangana (IN)

(73) Assignee: Laurus Labs Private Ltd, Telangana (IN)

( * ) Notice: Subject to any disclaimer, the term of this patent is extended or adjusted under 35 U.S.C. 154(b) by 0 days.

(21) Appl. No.: 16/060,681

(22) PCT Filed: Dec. 9, 2016

(86) PCT No.: PCT/GB2016/053875
§ 371 (c)(1),
(2) Date: Jun. 8, 2018

(87) PCT Pub. No.: WO2017/098252
PCT Pub. Date: Jun. 15, 2017

(65) Prior Publication Data
US 2018/0362571 A1    Dec. 20, 2018

(30) Foreign Application Priority Data

Dec. 11, 2015  (IN) .......................... 6635/CHE/2015
Feb. 8, 2016   (GB) ................................. 1602185.9

(51) Int. Cl.
| | | |
|---|---|---|
| C07H 19/06 | (2006.01) | |
| C07H 1/00 | (2006.01) | |
| C07F 9/22 | (2006.01) | |
| A61P 35/00 | (2006.01) | |

(52) U.S. Cl.
CPC ............ *C07H 19/06* (2013.01); *C07F 9/222* (2013.01); *C07H 1/00* (2013.01); *A61P 35/00* (2018.01); *C07B 2200/07* (2013.01)

(58) Field of Classification Search
CPC ........... C07H 1/00; C07H 19/06; C07F 9/222; C07B 2200/07; A61P 35/00
See application file for complete search history.

(56) References Cited

U.S. PATENT DOCUMENTS

| | | | | |
|---|---|---|---|---|
| 7,951,787 B2 | 5/2011 | McGuigan | | |
| 8,618,076 B2* | 12/2013 | Ross | ...................... | C07H 19/06 514/51 |
| 8,629,263 B2* | 1/2014 | Ross | ...................... | C07H 19/10 536/25.3 |
| 8,633,309 B2* | 1/2014 | Ross | ...................... | C07H 19/10 536/28.53 |
| 8,642,756 B2 | 2/2014 | Ross et al. | | |
| 8,735,569 B2* | 5/2014 | Ross | ...................... | C07H 19/06 536/25.33 |
| 8,859,756 B2* | 10/2014 | Ross | ...................... | C07F 7/1804 536/26.1 |
| 9,206,217 B2* | 12/2015 | Ross | ...................... | C07H 19/10 |
| 9,284,342 B2* | 3/2016 | Ross | ...................... | C07H 19/06 |
| 9,834,577 B2 | 12/2017 | Dammalapati et al. | | |
| 10,005,810 B2 | 6/2018 | McGuigan et al. | | |
| 10,117,888 B2 | 11/2018 | Griffith et al. | | |
| 10,538,541 B2* | 1/2020 | Yuan | ...................... | C07F 9/222 |
| 2011/0245484 A1 | 10/2011 | Ross et al. | | |
| 2011/0251152 A1 | 10/2011 | Ross et al. | | |
| 2017/0107246 A1 | 4/2017 | Griffith et al. | | |
| 2017/0226147 A1 | 8/2017 | Griffith | | |
| 2018/0237466 A1 | 8/2018 | Yuan et al. | | |
| 2018/0244701 A1 | 8/2018 | Yuan et al. | | |
| 2018/0244710 A1 | 8/2018 | Yuan et al. | | |
| 2018/0271889 A1 | 9/2018 | Griffith | | |
| 2018/0273575 A1 | 9/2018 | McGuigan et al. | | |
| 2018/0289733 A1 | 10/2018 | Griffith et al. | | |
| 2019/0022118 A1 | 1/2019 | Griffith et al. | | |

FOREIGN PATENT DOCUMENTS

| | | |
|---|---|---|
| WO | WO-2005/012327 A2 | 2/2005 |
| WO | WO-2011/123645 A2 | 10/2011 |
| WO | WO-2012/012465 A1 | 1/2012 |
| WO | WO-2012/075140 A1 | 6/2012 |
| WO | WO-2013/187978 A1 | 12/2013 |
| WO | WO-2014/076490 A1 | 5/2014 |
| WO | WO-2015/198058 A1 | 12/2015 |
| WO | WO-2015/198059 A1 | 12/2015 |
| WO | WO-2016/012781 A1 | 1/2016 |
| WO | WO-2016/030335 A1 | 3/2016 |
| WO | WO-2016/055769 A1 | 4/2016 |
| WO | WO-2016/181093 A1 | 11/2016 |
| WO | WO-2017/060661 A1 | 4/2017 |
| WO | WO-2017/098252 A1 | 6/2017 |
| WO | WO-2017/109444 A1 | 6/2017 |
| WO | WO-2017/109485 A1 | 6/2017 |
| WO | WO-2017/109486 A1 | 6/2017 |
| WO | WO-2018/229493 A2 | 12/2018 |

OTHER PUBLICATIONS

U.S. Appl. No. 15/279,611, McGuigan.
International Search Report and Written Opinion for International Application No. PCT/GB2004/003148 dated Jan. 20, 2005.
Slusarczyk et al., "Application of ProTide Technology to Gemcitabine: A Successful Approach to Overcome the Key Cancer Resistance Mechanicms Leads to a New Agent (NUC-1031) in Clinical Development," Journal of Medicinal Chemistry, 57(4): 1531-1542 (2014).
International Search Report and Written Opinion for International Application PCT/GB2016/053875 dated Feb. 16, 2017.
Ross et al., "Synthesis of Diasteromericlly Pure Nucleotide Phosphoramidates," The Journal of Organic Chemistry, 76(20): 8311-8319 (2011).
Cho et al., "Efficient Synthesis of Exo-N-carbamoyl Nucleosides: Application to the Synthesis of Phosphoramidate Prodrugs," Organic Letters, 14(10):2488-2491 (2012).

(Continued)

*Primary Examiner* — Lawrence E Crane
(74) *Attorney, Agent, or Firm* — Dana M. Gordon; Foley Hoag LLP

(57) ABSTRACT

Disclosed is a method for the preparation of intermediates useful in the synthesis of gemcitabine-[phenyl-benzoxy-L-alaninyl)]-phosphate. Also disclosed is a method of preparing gemcitabine-[phenyl-benzoxy-L-alaninyl)]-phosphate.

26 Claims, No Drawings

(56) References Cited

OTHER PUBLICATIONS

Cho et al., "Efficient synthesis of nucleoside aryloxy phosphoramidate prodrugs utilizing benzylocarbonyl protection," Tetrahedron, 67(30):5487-5493 (2011).

McGuigan, "A phosphoramidate ProTide (NUC-1031) and acquired and intrinsic resistance to gemcitabine," J Clin Oncol, 29:E13540 (2011).

* cited by examiner

DIASTEREOSELECTIVE SYNTHESIS OF PHOSPHATE DERIVATIVES

RELATED APPLICATIONS

This application is a § 371 national stage application based on Patent Cooperation Treaty Application serial number PCT/GB2016/053875, filed Dec. 9, 2016; which claims the benefit of priority to India Patent Application No. IN 6635/CHE/2015, filed Dec. 11, 2015; and United Kingdom Patent Application No. GB 1602185.9, filed Feb. 8, 2016.

FIELD OF THE INVENTION

The present invention generally relates to a novel process for the preparation of gemcitabine-[phenyl-benzoxy-L-alaninyl)]-phosphate, using novel phosphoramidate intermediates.

BACKGROUND OF THE INVENTION

A number of nucleoside analogs such as cytarabine, fludarabine, cladribine, capecitabine, gemcitabine and pentostatin are used clinically as highly effective anti-neoplastic agents. Among these, gemcitabine (2',2'-difluoro-2'-deoxycytidine; marketed as Gemzar™) is of particular interest due to its unique activity against solid tumors. It is currently approved to treat breast, non-small cell lung, ovarian and pancreatic cancers and widely used to treat a variety of other cancers including bladder, biliary, colorectal and lymphoma.

Several self-potentiating mechanisms unique to this nucleoside analog are believed responsible for the activity of gemcitabine against solid tumors. The diphosphate metabolite of gemcitabine inhibits ribonucleotide reductase, which results in lower concentrations of intracellular deoxycytidine triphosphate (dCTP) and thus, increased incorporation of the triphosphate gemcitabine metabolite into DNA, which results in inhibition of DNA synthesis and blocks completion of the cell division cycle. Additionally, reduction in dCTP concentration up regulates the enzyme cytidine kinase, which is responsible for initial phosphorylation of gemcitabine, a necessary step in the inhibition of DNA synthesis by the drug. Finally, the triphosphate metabolite of gemcitabine is an inhibitor of cytidine deaminase, which is responsible for gemcitabine inactivation by conversion to the uridine metabolite. Accordingly, the additive nature of the above factors may explain the efficacy of gemcitabine in treating solid tumors.

Due to the lipophilic nature of the ProTides, these molecules can deliver nucleoside monophosphates directly in to the intact tumor cell. Previous studies have characterized multiple cellular transport mechanisms for nucleoside analog drugs and their derivatives (for a review, see Balimane et al., *Adv. Drug Delivery Rev.* 1999, 39, 183-209). A relatively hydrophilic compound, gemcitabine has limited ability to permeate plasma membranes via passive diffusion and several studies have demonstrated that gemcitabine is a substrate for equilibrative and concentrative nucleoside transporters (ENT's and CNT's respectively). Specifically, gemcitabine is transported by human ENT1, ENT2, CNT1 and CNT3, but not the purine-selective concentrative transporter CNT2 (see Mackey et al., *Cancer Res.* 1998, 58, 4349-4357; Mackey et al., *J. Natl. Cancer Inst.* 1999, 91, 1876-1881; and Fang et al., *Biochem. J.* 1996, 317, 457465).

U.S. Pat. No. 4,808,614 discloses 2,2'-difluoronucleosides which are known anti-viral and anti-tumor agents, in particular 2',2'-difluoro-2'-deoxycytidine (commonly known as Gemcitabine).

U.S. Pat. No. 7,951,787 discloses phosphoramidate derivatives of nucleotides such as 2'-deoxy-2',2'-difluoro-D-cytidine-5'-O-[phenyl(benzoxy-L-alaninyl)] phosphate (also referred to as Gemcitabine-[phenyl(benzoxy-L-alaninyl)] phosphate or NUC-1031). Methods for chemically synthesizing these derivatives are disclosed in this patent by reacting gemcitabine or its structural variants with a diastereoisomeric mixture of phosphochloridate such as phenyl-(benzoxy-L-alaninyl)-phosphorochloridate of Formula II in the presence of N-methylimidazole followed by purification of the product by column chromatography, eluting with dichloromethane/methanol 95:5 to give pure product as a white foamy solid with very low yield of 16%.

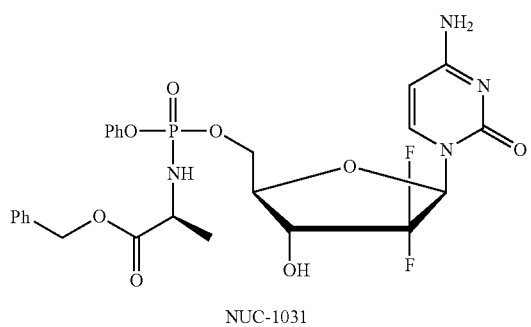

NUC-1031

NUC-1031 is typically prepared as a mixture of two diastereoisomers, epimeric at the phosphate centre. The diastereoisomers of NUC-1031 have the following structures:

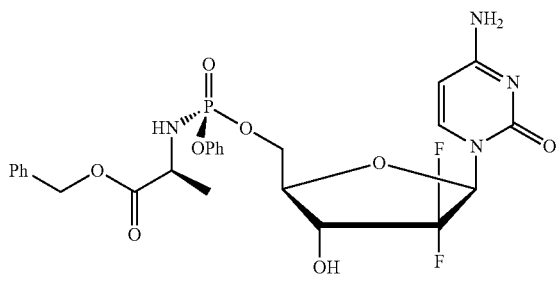

(S)-NUC-1031

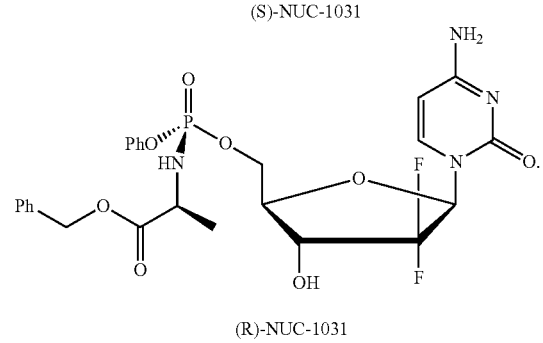

(R)-NUC-1031

NUC-1031 is extremely lipophillic and thus poorly water soluble (by calculation: <0.1 mg/mL), and the ionisable moieties have calculated pKas which lie out-side the pH range suitable for parenteral administration. It is essentially insoluble in water, regardless of salt content or pH, and this has implications for the development of formulations for delivering the compound at sufficiently high dosages for effective treatment. It also has implications for the development of efficient manufacturing processes which will allow NUC-1031 to be produced cost effectively.

It has recently been discovered that the (S)-epimer of gemcitabine-[phenyl-benzoxy-L-alaninyl)]-phosphate has sufficient solubility in mixtures of a number of polar organic solvents with water to render it suitable for formulation and administration as a therapeutic agent. The solubility of the (R)-epimer is considerably lower. In certain solvent mixtures the difference in solubility between the (S)-epimer and the (R)-epimer is over 100 fold. It is expected therefore that more clinically effective, practical and patient friendly administration methods can be developed using the (S)-epimer than can be developed using the (R)-epimer or using the mixture. It is thus desirable to be able to provide gemcitabine-[phenyl-benzoxy-L-alaninyl)]-(S)-phosphate in substantially diastereoisomerically pure form.

The low solubility of NUC-1031 in many solvents, particularly those commonly used in separating compounds using HPLC, mean that large volumes of solvent would be needed for any HPLC based separation. This means that any HPLC based industrial scale separation process would be high cost, consume large amounts of energy and material and produce large amounts of waste.

Although it appears preferable at the time of filing this application to administer gemcitabine-[phenyl-benzoxy-L-alaninyl)]-phosphate as the (S)-epimer, one can also conceive of reasons for needing to obtain the (R)-epimer in a diastereoisomerically pure form. These would include the carrying out of comparative tests, to convert the (R)-epimer to the (S)-epimer or because the (R)-epimer provides benefits over the (S)-epimer which outweigh its low solubility.

Indeed the (R)-epimer has been shown to have a half-life on incubation with isolated human hepatic cells which is four times that of the (S)-epimer. The longer half-life associated with (R)-isomer indicates a lower intrinsic clearance and should result in a different pharmacokinetic and pharmacodynamic profile to the (S)-isomer which may offer some benefits.

Both (S)- and (R)-epimers are therapeutically active.

WO 2014/076490 discloses a process for preparation of nucleoside prodrugs such as Gemcitabine-[phenyl(benzoxy-L-alaninyl)] phosphate by reacting gemcitabine or its structural variants with a diastereoisomeric mixture of phosphochloridates in the presence of a catalyst comprising metal salt such as $Cu(OTf)_2$, CuCl, CuBr, CuI, $Cu(OAc)_2$, $CuSO_4$, $Cu(OC(O)CF_3)_2$, $Me(OTf)_3$, $Cu(OTf)_2$, $Yb(OTf)_3$, $Fe(OTf)_3$, $La(OTf)_3$ with yield of 45%.

It is an aim of certain embodiments of this invention to provide a method of providing gemcitabine-[phenyl-benzoxy-L-alaninyl)]-(S)-phosphate in substantially diastereoisomerically pure form.

It is an aim of certain embodiments of this invention to provide a method of providing gemcitabine-[phenyl-benzoxy-L-alaninyl)]-(R)-phosphate in substantially diastereoisomerically pure form.

It is an aim of certain embodiments of this invention to provide a method of providing the (S) and/or (R)-epimer(s) in substantially diastereoisomerically pure form(s) which is scalable, economic and/or efficient, e.g. more scalable, economic and/or efficient than methods using HPLC. Thus, it is an aim of certain embodiments of this invention to provide a method of providing the (S) and/or (R)-epimer(s) in substantially diastereoisomerically pure form(s) which is suitable for large scale manufacture.

It is an aim of certain embodiments of this invention to provide a simple method i.e. a method which involves a minimum number of process steps and or reagents of providing the (S) and/or (R)-epimer(s) in substantially diastereoisomerically pure form(s).

Another aim of certain embodiments of this invention is to provide a method which ensures the separated (S)- or (R)-epimer are provided in substantially diastereoisomerically pure form and at the same time meet or exceed the necessary criteria stipulated by organisations such as the US FDA concerning the amounts and nature of any trace impurities which arise from synthesis and separation.

Certain embodiments of this invention satisfy some or all of the above aims.

SUMMARY OF THE INVENTION

In accordance with a first aspect of the invention there is provided a process for the preparation of gemcitabine-[phenyl (benzoxy-L-alaninyl)] phosphate (Formula I) in substantially diastereoisomerically pure form:

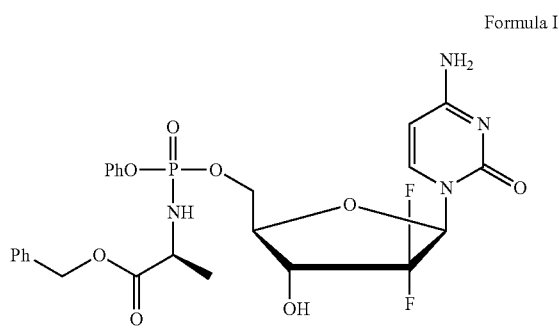

Formula I the process comprising step a) and optionally step b):
a) reacting a compound of Formula II; wherein $R^1$ represents an electron withdrawing group and a is an integer from 1 to 5, with a compound of Formula III in presence of a base (B1) to provide a compound of Formula IV in substantially diastereomerically pure form; wherein $P^1$, $P^2$ and $P^3$ independently represents hydrogen or a protecting group; and wherein the compound of formula II is in substantially diastereomerically pure form:

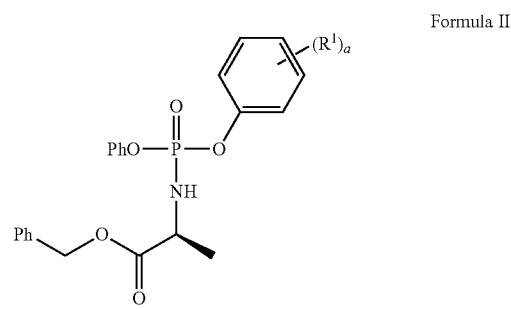

Formula II

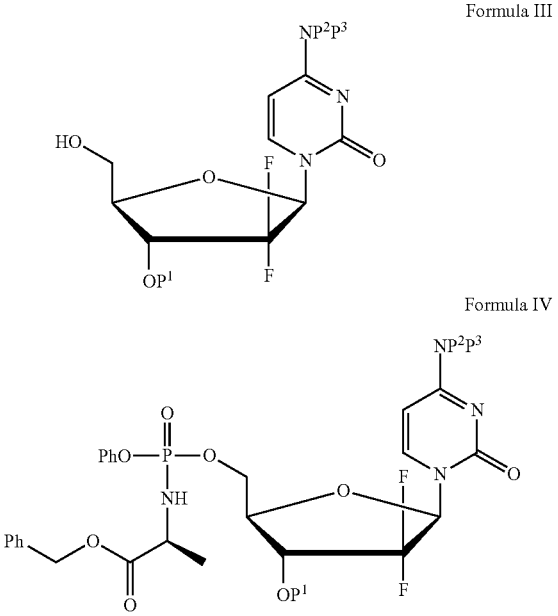

Formula III

Formula IV b) where any one or more of P¹, P² and P³ are protecting groups, optionally removing the protecting groups P¹, P² and P³ from the compound of formula IV to provide gemcitabine-[phenyl (benzoxy-L-alaninyl)] phosphate in substantially diastereomerically pure form.

R¹ may be selected from the group comprising: halo group (e.g. selected from fluoro, bromo, chloro or iodo); trifluoromethyl, cyano and nitro. a is an integer between 1 and 5. R¹ may be at each occurrence halo, e.g. fluoro. a may be 5.

Displacement of the substituted phenoxy group takes place with inversion of phosphate stereochemistry. Thus, the (S)-diastereoisomer of the precursor provides the (S)-diastereoisomer of NUC-1031 and the (R)-diastereoisomer of the precursor provides the (R)-diastereoisomer of NUC-1031.

Thus, it may be that the process of the first aspect is a method of making the (S)-diastereoisomer of NUC-1031 in diastereomerically enriched form and the compound of formula II is the (S)-diastereoisomer in diastereomerically enriched form.

The base (B1) might be a nitrogen base. Nitrogen bases include N-alkylimidazoles, (e.g. N-methyl imidazole (NMI)), imidazole, optionally substituted pyridines, (e.g. collidine, pyridine, 2,6-lutidine) and trialkylamines (e.g. triethylamine, and diisopropylethylamine). Alternatively, the base (B1) may be an organometallic base or metal hydride base (e.g. NaH). Thus, the base may be a Grignard reagent (i.e. an alkylmagnesium halide). Exemplary Grignard reagents include t-butylmagnesium halides such as tBuMgCl, tBuMgBr. Preferably, the base is tBuMgCl.

The process may be carried out in a solvent S1.

In a second aspect of the invention, there is provided a process for the diastereoisomeric enrichment of a compound of Formula II; the process comprising:

c) suspending or dissolving the R-diastereoisomer of the compound of Formula II or a mixture of the (R)- and (S)-diastereoisomers of the compound of Formula II in a solvent (S2), d) treating the solution or suspension with a base (B2) to obtain (S)-diastereoisomer in substantially diastereomerically pure form, and e) isolating the (S)-diastereoisomer of Formula II.

The inventors have surprisingly found that upon treating compounds of formula II with a base, they isomerise, preferentially forming the (S)-diastereoisomer over the (R)-diastereoisomer. Thus, the (R)-diastereoisomer can be converted to the (S)-diastereoisomer or an epimeric mixture of the (R)-diastereoisomer and the (S)-diastereoisomer can be converted to the (S)-diastereoisomer. This increases the net efficiency of any synthetic sequence for making the (S)-diastereoisomer of NUC-1031 which incorporates the process of the first aspect as it means that all of the compound of formula II, even that which originally formed as the (R)-diastereoisomer can be used and none of it is discarded.

It may be that the process comprises:

forming the compound of Formula II as a mixture of the (R)- and (S)-diastereoisomers; and that step c) comprises suspending or dissolving the mixture of the (R)- and (S)-diastereoisomers of the compound of Formula II in a solvent (S2).

The compound of formula II used in the process of the first aspect may be (S)-diastereoisomer formed according to the process of the second aspect.

The base (B2) may be selected from the group consisting of organic amine bases (e.g. primary, secondary, tertiary amines, cyclic amine; exemplary organic amine bases include bases include N-alkylimidazoles, (e.g. N-methyl imidazole (NMI), imidazole, optionally substituted pyridines, (e.g. collidine, pyridine, 2,6-lutidine) and trialkylamines (e.g. triethylamine, and diisopropylethylamine)); or inorganic bases (e.g. alkali metal hydroxide, alkali metal carbonates, alkali metal alkoxides, alkali metal arylxides). Preferably, B2 is a tertiary amine. Thus, B2 may be a trialkylamine. Most preferably, B2 is triethylamine.

The solvent S2 may be selected from the group consisting of amides, ethers, esters, ketones, aromatic hydrocarbons, halogenated solvents, nitriles, sulfoxides, sulfones and mixtures thereof. S2 may be an organic solvent. Organic solvents include but are not limited to ethers (e.g. tetrahydrofuran, dioxane, diethyl ether); ketones (e.g. acetone and methyl isobutyl ketone); halogenated solvents (e.g. dichloromethane, chloroform and 1,2-dichloroethane); hydrocarbons (e.g. cyclohexane, pentane, hexane, heptane), aromatic solvents (e.g. benzene and toluene), esters (e.g. ethyl acetate) and amides (e.g. DMF, NMP); or mixtures thereof. Preferably, S2 is a hydrocarbon or is a mixture comprising a hydrocarbon. Where S2 is a mixture, it may be a mixture that comprises over 50% (e.g. over 70%) of the hydrocarbon S2 may be a hydrocarbon. The hydrocarbon may be hexane. The hydrocarbon may be heptane. S2 may be a mixture of hexane or heptane and a polar organic solvent (e.g. an ether, ester, alcohol or halogenated solvent). S2 may be a mixture of hexane or heptane and a polar organic solvent, the mixture comprising over 50% (e.g. over 70%) by volume hexane or heptane. S2 may be a mixture of hexane or heptane and ethyl acetate. S2 may be a mixture of heptane and ethyl acetate. S2 may be a mixture of hexane or heptane and ethyl acetate, the mixture that comprising over 50% (e.g. over 70%) by volume hexane or heptane. S2 may be a mixture of heptane and ethyl acetate, the mixture comprising over 50% (e.g. over 70%) by volume heptane.

Step d) may involve stirring the mixture of the compound of formula II and the base B2 for 2 h or longer. Step d) may involve stirring the mixture of the compound of formula II and the base B2 for 6 h or longer. Step b) may involve stirring the mixture of the compound of formula II and the base B2 for 10 h or longer. Step d) may involve stirring the mixture of the compound of formula II and the base B2 for 16 h or longer. Step d) may involve stirring the mixture of the compound of formula II and the base B2 for up to 36 h.

Step d) may involve stirring the mixture of the compound of formula II and the base B2 at a temperature from 0 to 50° C. Step d) may involve stirring the mixture of the compound of formula II and the base B2 at a temperature from 10 to 35° C.

In certain specific embodiments, the compound of Formula II is a compound selected from:

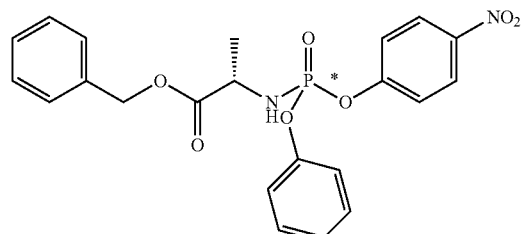

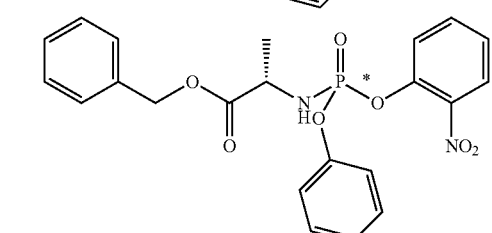

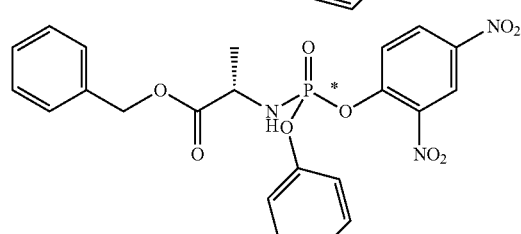

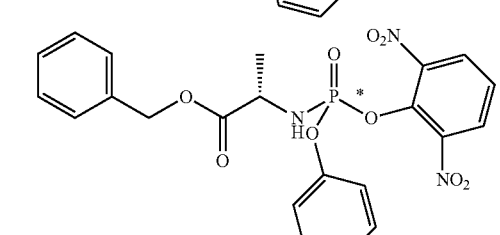

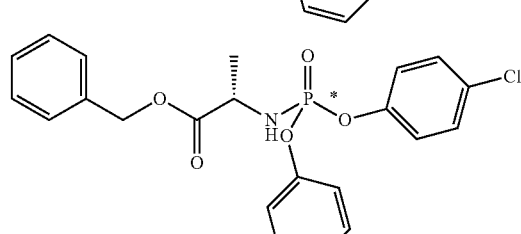

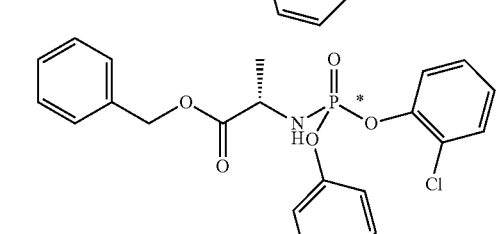

-continued

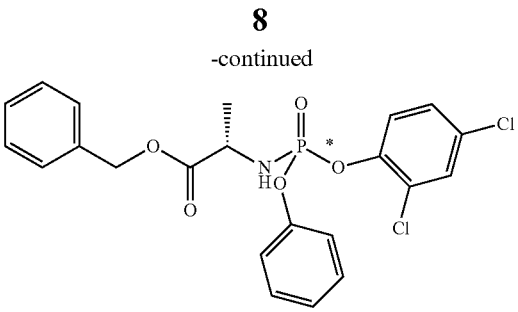

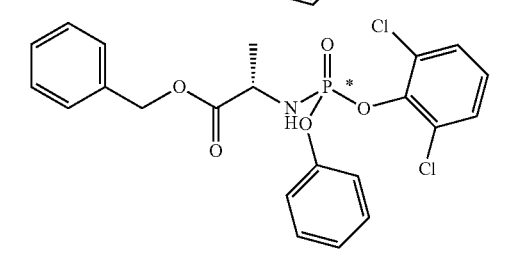

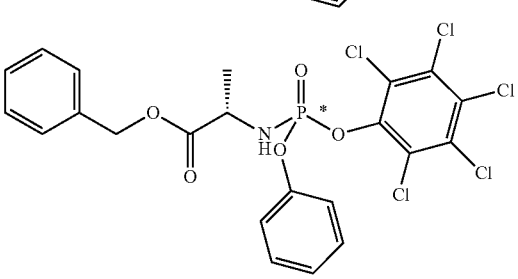

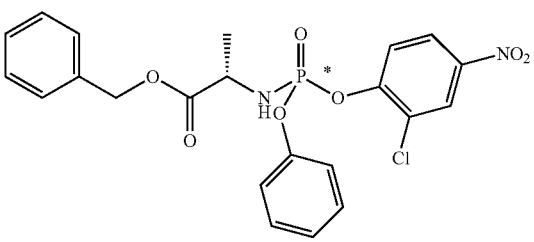

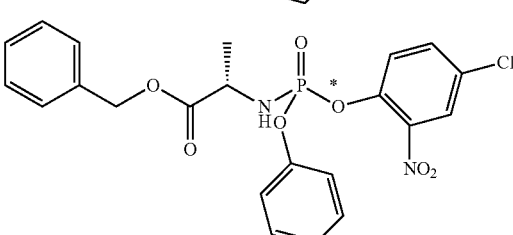

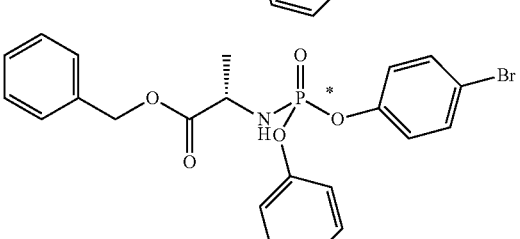

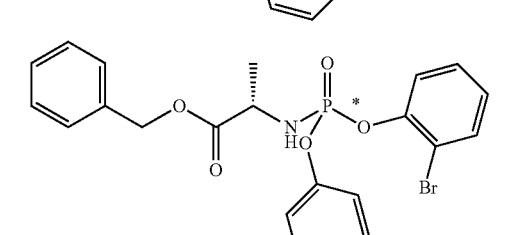

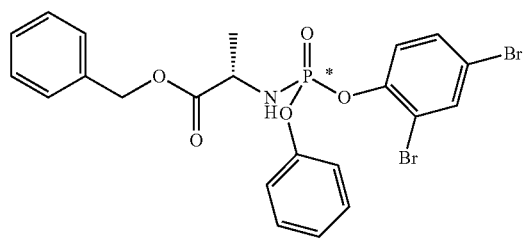
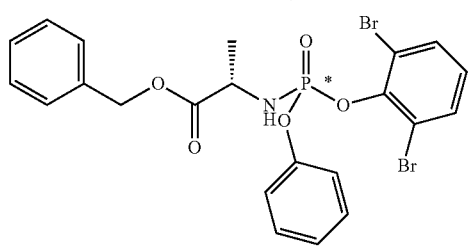
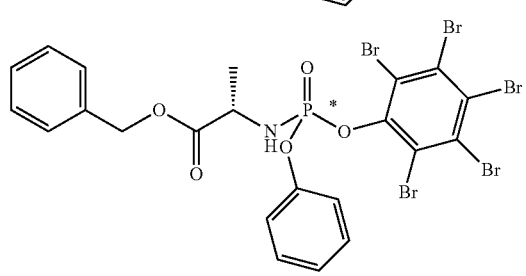
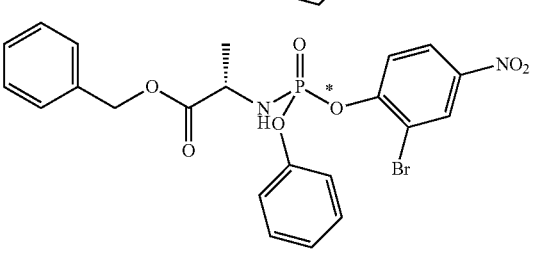
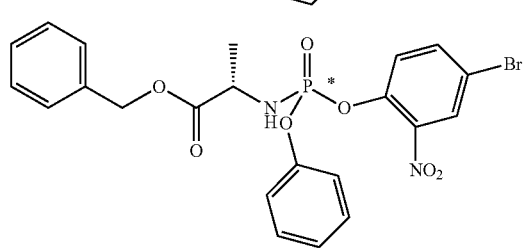
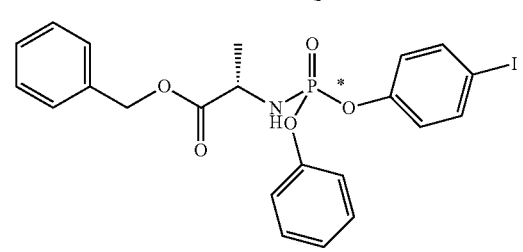
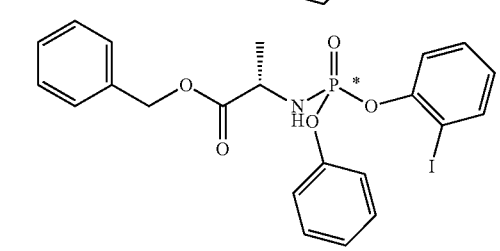
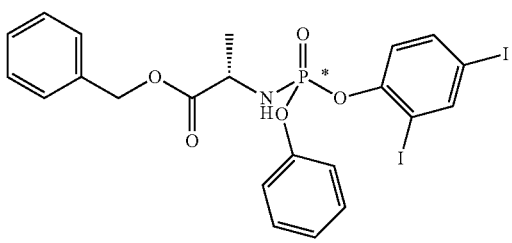
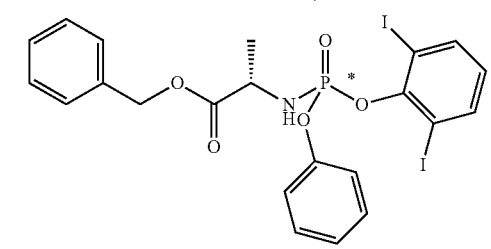
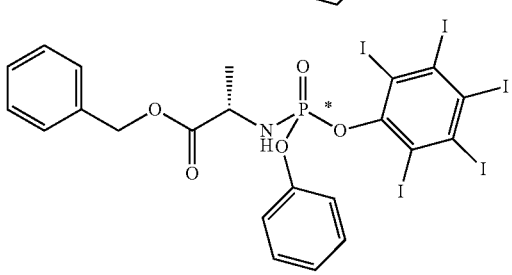
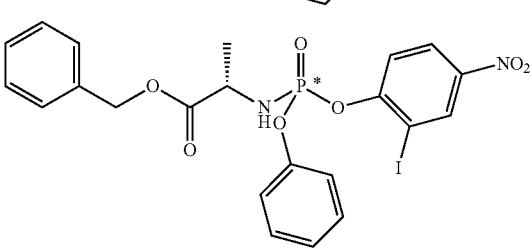
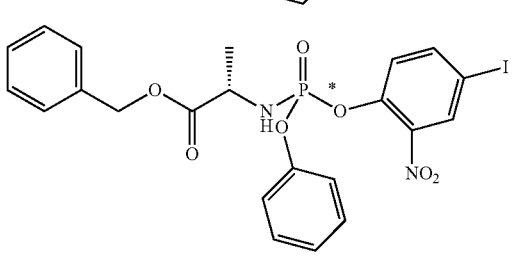
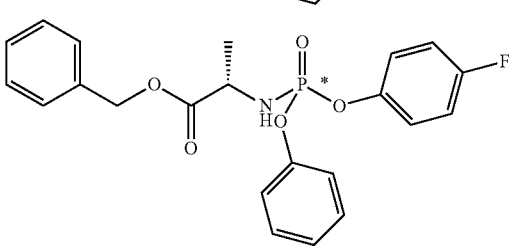
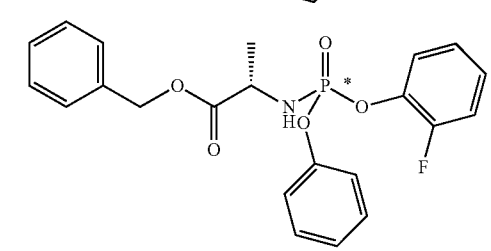

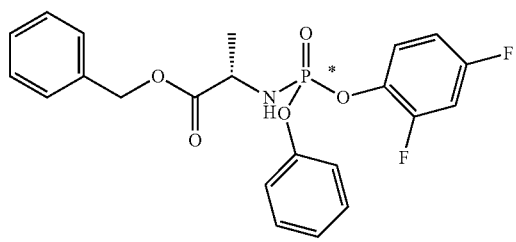
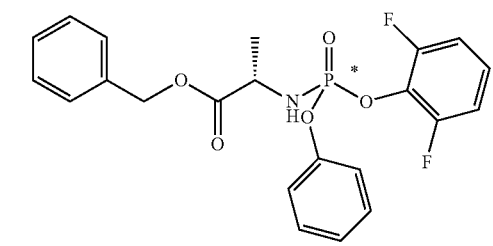
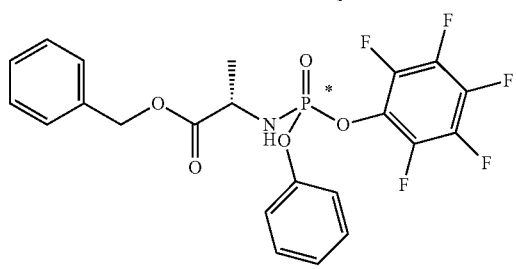
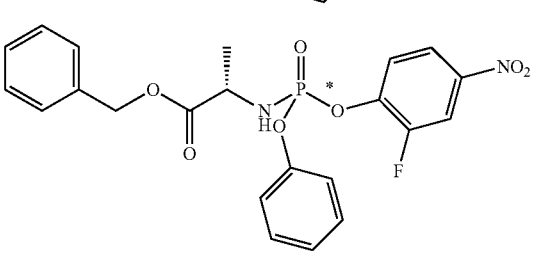
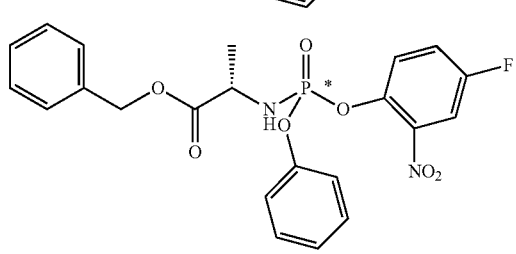
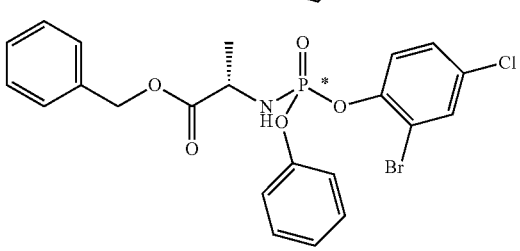
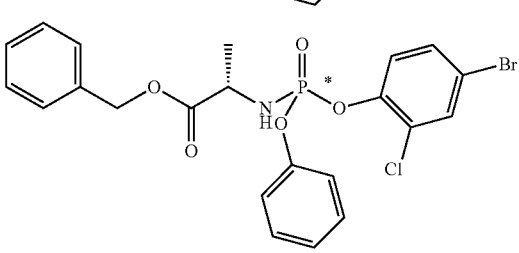
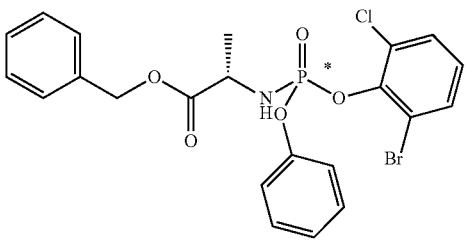
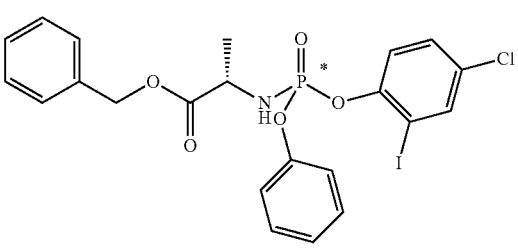
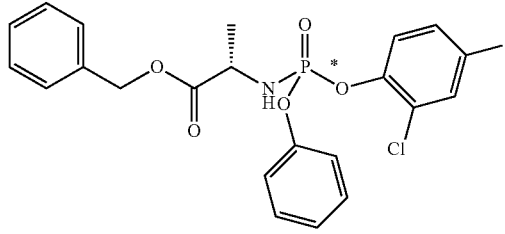
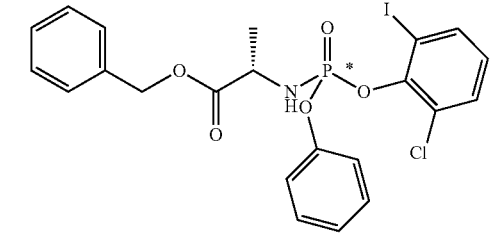
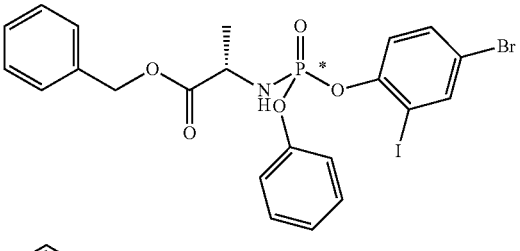
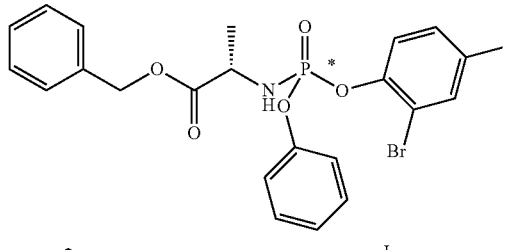
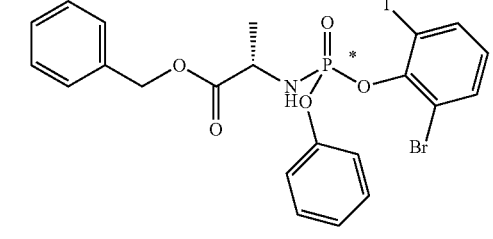

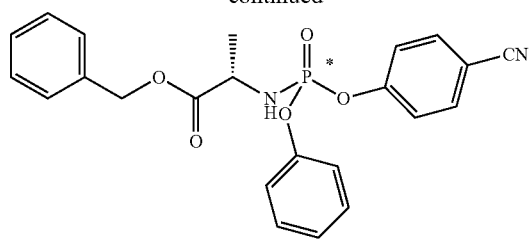
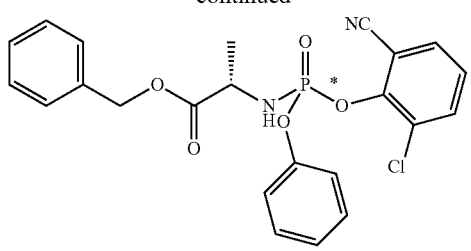
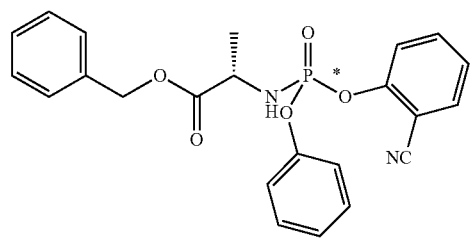
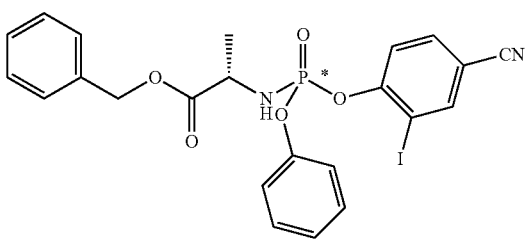
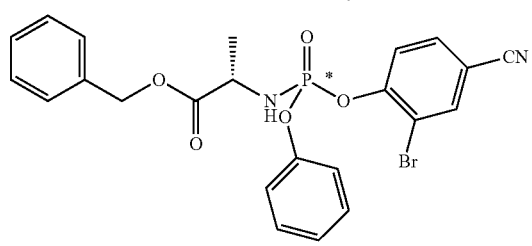
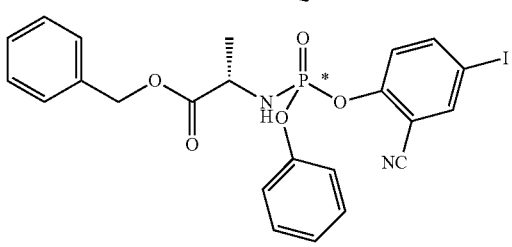
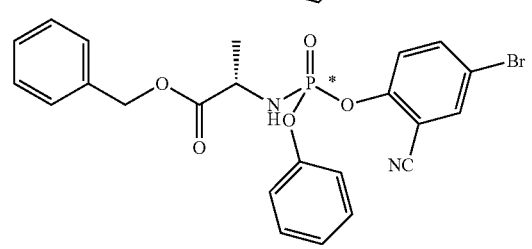
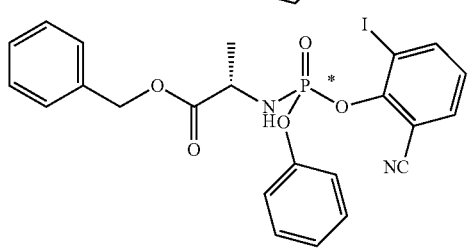
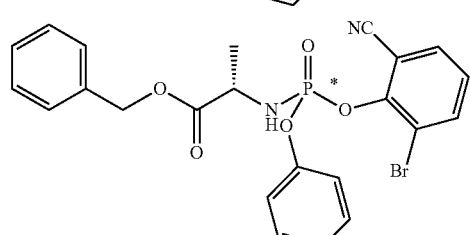
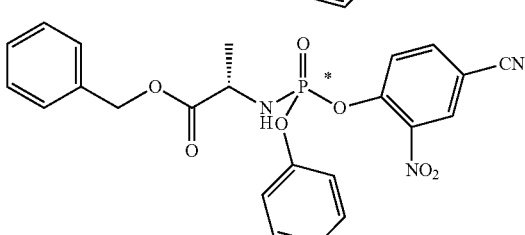
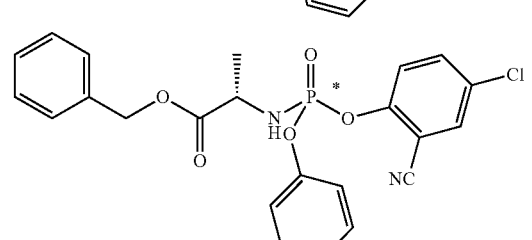
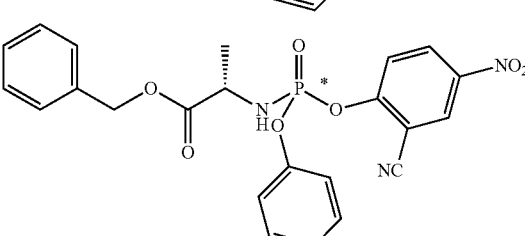
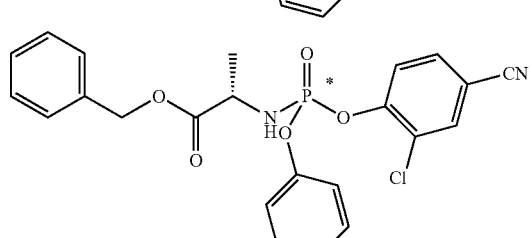
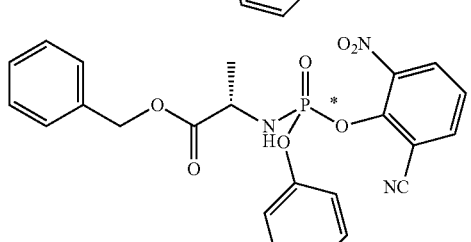

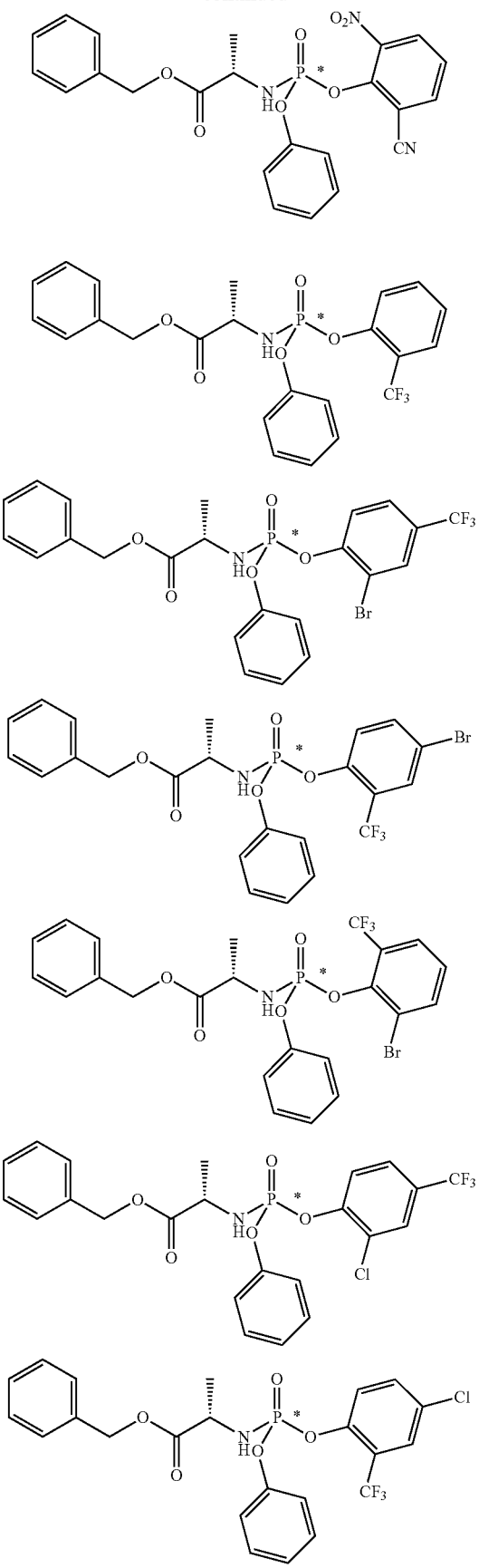
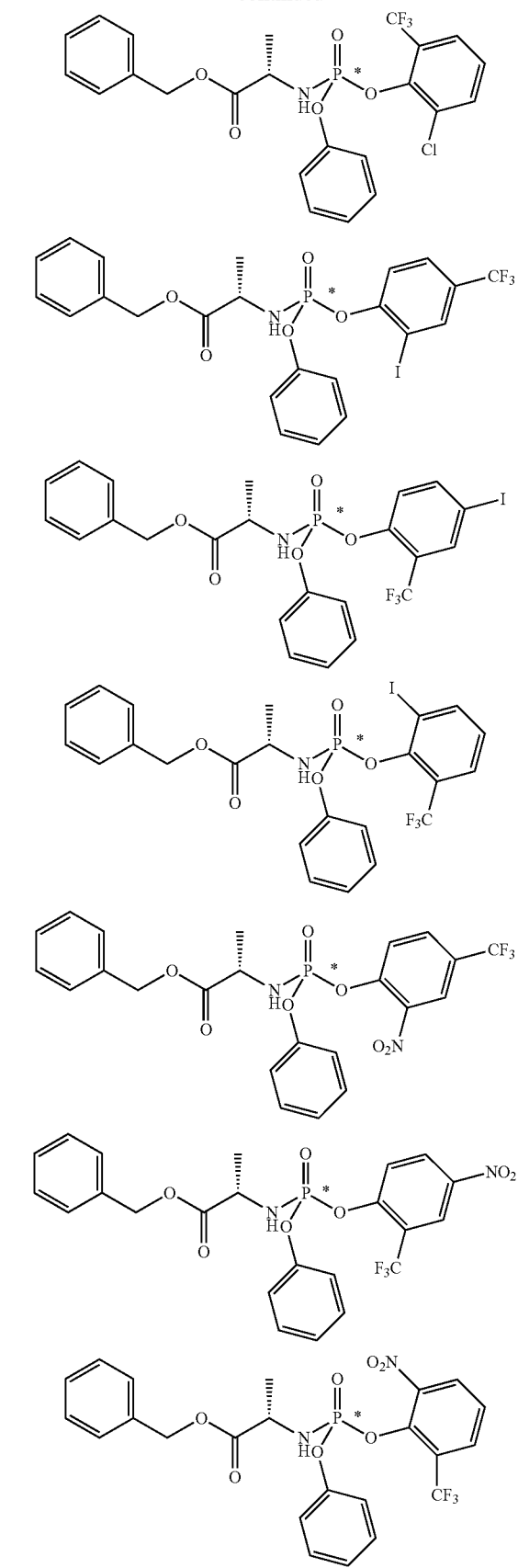

The compound of formula II may be:

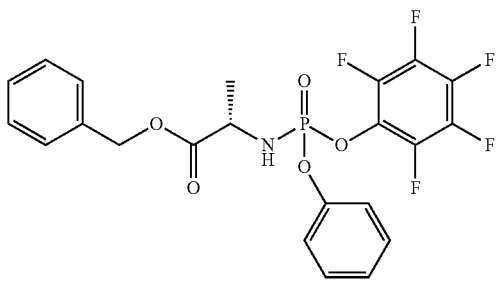 [SMILES: C[C@H](NP(=O)(Oc1ccccc1)Oc1c(F)c(F)c(F)c(F)c1F)C(=O)OCc1ccccc1]

The compound of formula II may be:

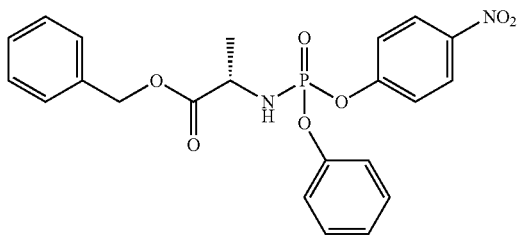 [SMILES: C[C@H](NP(=O)(Oc1ccccc1)Oc1ccc([N+](=O)[O-])cc1)C(=O)OCc1ccccc1]

A protecting group for a hydroxyl group (e.g. $P^1$) may be independently selected from optionally substituted —Si($C_{1-6}$alkyl)$_3$, optionally substituted —C(O)—$C_1$-$C_6$-alkyl, optionally substituted —C(O)-aryl, optionally substituted —C(O)—O$C_1$—$C_6$-alkyl, —C(O)—O— allyl, —C(O)—O—CH$_2$-fluorenyl, optionally substituted —CH(aryl)$_3$, optionally substituted —($C_1$-$C_3$-alkylene)-aryl, optionally substituted —C(O)OCH$_2$-aryl and —$C_1$-$C_4$-alkyl-O—$C_1$-$C_4$-alkyl.

A protecting group for an amino group (e.g. $P^2$ and/or $P^3$) may at each occurrence be independently selected from —C(O)O$C_1$—$C_6$-alkyl, optionally substituted —C(O) OCH$_2$-aryl, —C(O)—O-allyl, —C(O)—O—CH$_2$-fluorenyl, optionally substituted —CH(aryl)$_3$, optionally substituted —($C_1$-$C_3$-alkylene)-aryl, optionally substituted —C(O)—$C_1$-$C_6$-alkyl, optionally substituted —C(O)-aryl, —S(O)$_2$—$C_1$-$C_6$-alkyl, optionally substituted —S(O)$_2$-aryl and optionally substituted —Si($C_{1-6}$alkyl)$_3$.

Many of the protected starting compounds of Formula III are known in the art and/or can be prepared by known methods. For example starting compounds of Formula III may be synthesized from gemcitabine by protecting the 3'-hydroxy and 4-amino groups with suitable protecting groups. The protecting groups can typically be added and removed using conventional protecting group methodology, for example, as described in "Protective Groups in Organic Chemistry," edited by J W F McOmie (1973); "Protective Groups in Organic Synthesis," 2$^{nd}$ edition, T W Greene (1991); and "Protecting Groups", 3$^{rd}$ addition P. J Koscienski (1995).

It will typically be necessary to prepare the 3'-hydroxy and 4-amino group protected compounds by first protecting the 5'-hydroxy group of gemcitabine with a protecting group which is orthogonal to those which will be used to protect the 3'-hydroxy and 4-amino group (i.e. a group which can be removed without also removing the desired 3'-hydroxy and 4-amino groups). Simultaneously or subsequently, the 3'-hydroxy and 4-amino groups are protected with the desired protecting group(s) and the 5'-hydroxy protecting group can be removed to generate the compound of formula III. Certain protecting groups can be simultaneously introduced onto the 3'-hydroxy and 5'-hydroxy and optionally the 4-amino groups and then selectively removed from the 5' hydroxyl group without being removed from the 3'-hydroxy and the 4-amino groups.

According to some embodiments, $P^1$ is independently selected from optionally substituted —Si($C_{1-6}$alkyl)$_3$, optionally substituted —C(O)—$C_1$-$C_6$-alkyl, optionally substituted —C(O)-aryl, optionally substituted —C(O)—O$C_1$—$C_6$-alkyl, —C(O)—O-allyl, —C(O)—O—CH$_2$-fluorenyl, optionally substituted —CH(aryl)$_3$, optionally substituted —($C_1$-$C_3$-alkylene)-aryl, optionally substituted —C(O)OCH$_2$-aryl and —$C_1$-$C_4$-alkyl-O—$C_1$-$C_4$-alkyl.

$P^1$ may be independently selected from optionally substituted —Si($C_{1-6}$alkyl)$_3$, optionally substituted —C(O)—O$C_1$—$C_6$-alkyl and optionally substituted —C(O)OCH$_2$-aryl, —C(O)—O-allyl. Preferably, $P^1$ is selected from —C(O)O-tBu, —C(O)O-benzyl and —C(O)OCH$_2$-allyl. Thus, $P^1$ may be —C(O)OCH$_2$-aryl. $P^1$ may be —C(O)O-tBu.

Alternatively, $P^1$ may be independently selected from optionally substituted —C(O)—$C_1$-$C_6$-alkyl and optionally substituted —C(O)-aryl, e.g. $P^1$ may be independently selected from benzoyl and acetyl.

$P^2$ may be independently selected from —C(O)O$C_1$—$C_6$-alkyl, optionally substituted —C(O)OCH$_2$-aryl, —C(O)—O-allyl, —C(O)—O—CH$_2$-fluorenyl, optionally substituted —CH(aryl)$_3$, optionally substituted —($C_1$-$C_3$-alkylene)-aryl, optionally substituted —C(O)—$C_1$-$C_6$-alkyl, optionally substituted —C(O)-aryl, —S(O)$_2$—$C_1$-$C_6$-alkyl, optionally substituted —S(O)$_2$-aryl and optionally substituted —Si($C_{1-6}$alkyl)$_3$.

$P^2$ may be independently selected from —C(O)O$C_1$—$C_6$-alkyl, optionally substituted —C(O)OCH$_2$-aryl, —C(O)—O-allyl, optionally substituted —CH(aryl)$_3$, and optionally substituted —Si($C_{1-6}$alkyl)$_3$. Preferably, $P^2$ is selected from —C(O)O-tBu, —C(O)O— benzyl and —C(O)OCH$_2$-allyl. Thus, $P^2$ may be —C(O)OCH$_2$-aryl.

Alternatively, $P^2$ may be independently selected from optionally substituted —C(O)—$C_1$-$C_6$-alkyl and optionally substituted —C(O)-aryl, e.g. $P^2$ may be independently selected from benzoyl and acetyl.

In another alternative, $P^2$ is H.

Likewise, $P^3$ may be independently selected from H, —C(O)O$C_1$—$C_6$-alkyl, optionally substituted —C(O) OCH$_2$-aryl, —C(O)—O-allyl, —C(O)—O—CH$_2$-fluorenyl, optionally substituted —CH(aryl)$_3$, optionally substituted —($C_1$-$C_3$-alkylene)-aryl, optionally substituted —C(O)—$C_1$-$C_6$-alkyl, optionally substituted —C(O)-aryl, optionally substituted —S(O)$_2$-aryl and optionally substituted —Si ($C_{1-6}$ alkyl)$_3$.

Preferably, $P^3$ is H.

The group optionally substituted —Si($C_{1-6}$alkyl)$_3$ may be a —Si($C_{1-4}$alkyl)$_3$ group. The group is (i.e. the alkyl groups are) preferably unsubstituted. Illustrative examples include triethylsilyl and t-butyl-dimethylsilyl.

The group optionally substituted —C(O)—$C_1$-$C_6$-alkyl may be a —C(O)—$C_1$-$C_6$-alkyl group. The group (i.e. the alkyl group) is preferably unsubstituted. Illustrative examples include acetyl and propionyl.

The group optionally substituted —C(O)-aryl may be a —C(O)-phenyl group. The group (i.e. the phenyl group) is preferably unsubstituted. Illustrative examples include benzoyl.

The group optionally substituted —C(O)—O$C_1$—$C_6$-alkyl may be a —C(O)—O$C_1$—$C_4$-alkyl group. The group (i.e. the alkyl group) is preferably unsubstituted. Illustrative examples include —C(O)—O-methyl and —C(O)—O-ethyl. A particularly preferred example is C(O)OtBu.

The group optionally substituted —(C$_1$-C$_3$-alkylene)-aryl is preferably an optionally substituted benzyl group. Illustrative examples include benzyl, phenethyl, 4-methoxy benzyl, 4-nitrobenzyl, 4-bromobenzyl, 2,3-dimethoxybenzyl and 2,4-dimethoxybenzyl.

The group optionally substituted —C(O)OCH$_2$-aryl is preferably an optionally substituted —C(O)Obenzyl group. Illustrative examples include —C(O)Obenzyl and —C(O)O-(4-methoxybenzyl).

The group optionally substituted —C$_1$-C$_4$-alkyl-O—C$_1$-C$_4$-alkyl may be a —C$_1$-C$_2$-alkyl-O—C$_1$-C$_2$-alkyl group. The group is (i.e. the alkyl groups are) preferably unsubstituted. Illustrative examples include methoxy-methyl (MOM) and 2-methoxy-ethoxy-methyl (MEM).

The group optionally substituted —S(O)$_2$—C$_1$-C$_6$-alkyl may be a —S(O)$_2$—C$_1$-C$_4$-alkyl group. The group (i.e. the alkyl group) is preferably unsubstituted. Illustrative examples include methanesulfonate.

The group optionally substituted —S(O)$_2$-aryl may be a —S(O)$_2$-phenyl group. Illustrative examples include phenylsulfonate, 4-methylphenylsulfonate and 4-nitro phenylsulfonate.

The group optionally substituted —CH(aryl)$_3$ may be a —CH(phenyl)$_3$ group. Illustrative examples include trityl.

Where two or more of P$^1$, P$^2$ and P$^3$ are protecting groups, the deprotection step may comprise two or three individual deprotection reactions. This is the case where two or three different protecting groups are used and where those two or three protecting groups cannot be removed under the same conditions.

It may be, however, that the deprotection step comprises a single deprotection reaction in which all protecting groups are removed. Thus, it may be that P$^1$ and P$^2$ are protecting groups which can be removed under the same conditions. It may be that P$^1$ and P$^2$ are the same.

It may be that both P$^1$ and P$^2$ are a group selected from optionally substituted —C(O)OC$_1$-C$_6$-alkyl, —C(O)—O-allyl and optionally substituted —C(O)OCH$_2$-aryl. Thus, both P$^1$ and P$^2$ may be a group selected from C(O)OtBu, —C(O)—O-allyl and C(O)O— benzyl. In some embodiments, P$^1$ and P$^2$ are both C(O)OtBu groups.

Preferably P$^3$ is hydrogen. Thus, in a particular embodiment, P$^1$ and P$^2$ are the same groups and P$^3$ is hydrogen. Thus, in a particular embodiment, P$^1$ and P$^2$ are both C(O)OtBu groups and P$^3$ is hydrogen.

It may be that P$^2$ and P$^3$ are each H and P$^1$ is a protecting group. It may be that P$^2$ and P$^3$ are each H and P$^1$ is a protecting group selected from —C(O)O-tBu, —C(O)O—benzyl and —C(O)OCH$_2$-allyl. It may be that P$^2$ and P$^3$ are each H and P$^1$ is —C(O)O-tBu.

Throughout this specification, 'diastereomerically enriched form' and 'substantially diastereomerically pure form' means a diastereoisomeric purity of greater than 95%. 'Diastereomerically enriched form' and 'substantially diastereomerically pure form' may mean a diastereoisomeric purity of greater than 98%, greater than 99% or greater than 99.5%.

Any of the aforementioned alkyl and aryl (e.g. phenyl, including the phenyl groups in benzyl groups) groups, are optionally substituted, where chemically possible, by 1 to 3 substituents which are each independently at each occurrence selected from the group consisting of: oxo, =NR$^a$, =NOR$^a$, halo, nitro, cyano, NR$^a$R$^a$, NR$^a$S(O)$_2$R$^a$, NR$^a$CONR$^a$R$^a$, NR$^a$CO$_2$R$^a$, OR$^a$; SR$^a$, SOR$^a$, SO$_3$R$^a$, SO$_2$R$^a$, SO$_2$NR$^a$R$^a$, CO$_2$R$^a$ C(O)R$^a$, CONR$^a$R$^a$, C$_2$-C$_4$-alkenyl, C$_2$-C$_4$-alkenyl, and C$_1$-C$_4$ haloalkyl; wherein R$^a$ is independently at each occurrence selected from H, C$_1$-C$_4$ alkyl and C$_1$-C$_4$ haloalkyl.

It may be that any of the aforementioned alkyl groups is unsubstituted.

It may be that any of the aforementioned aryl groups (e.g. phenyl, including the phenyl groups in benzyl groups) is optionally substituted, where chemically possible, by 1 to 3 substituents which are each independently at each occurrence selected from the group consisting of: halo, nitro, cyano, NR$^a$R$^a$, NR$^a$S(O)$_2$R$^a$, NR$^a$CONR$^a$R$^a$, NR$^a$CO$_2$R$^a$, OR$^a$; SR$^a$, SOR$^a$, SO$_3$R$^a$, SO$_2$R$^a$, SO$_2$NR$^a$R$^a$, CO$_2$R$^a$ C(O) R$^a$, CONR$^a$R$^a$, C$_1$-C$_4$-alkyl, C$_2$-C$_4$-alkenyl, C$_2$-C$_4$-alkenyl, and C$_1$-C$_4$ haloalkyl; wherein R$^a$ is independently at each occurrence selected from H, C$_1$-C$_4$ alkyl and C$_1$-C$_4$ haloalkyl.

It may be that any of the aforementioned aryl (e.g. phenyl, including the phenyl groups in benzyl groups) groups is optionally substituted by 1 to 3 substituents which are each independently at each occurrence selected from the group consisting of: halo, nitro, OR$^a$; C$_1$-C$_4$ haloalkyl; wherein R$^a$ is independently at each occurrence selected from H, C$_1$-C$_4$ alkyl and C$_1$-C$_4$ haloalkyl.

Aryl groups have from 6 to 20 carbon atoms as appropriate to satisfy valency requirements. Aryl groups are carbocyclic groups which satisfy the Huckel rule (i.e. they contain a carbocyclic ring system containing 2(2n+1)π electrons). Aryl groups may be optionally substituted phenyl groups, optionally substituted biphenyl groups, optionally substituted naphthalenyl groups or optionally substituted anthracenyl groups. Equally, aryl groups may include non-aromatic carbocyclic portions. Preferably an aryl group is an optionally substituted phenyl group.

Alkyl groups may be straight chain or branched. Thus, for example, a C$_4$ alkyl group could be n-butyl, i-butyl or t-butyl.

Step a) of the first aspect may be conducted in an organic solvent (S1). Organic solvents include but are not limited to ethers (e.g. tetrahydrofuran, dioxane, diethyl ether); ketones (e.g. acetone and methyl isobutyl ketone); halogenated solvents (e.g. dichloromethane, chloroform and 1,2-dichloroethane); and amides (e.g. DMF, NMP); or mixtures thereof. Where step a) is conducted in the presence of a Grignard reagent, the organic solvent is preferably an ether. Most preferably, the solvent is tetrahydrofuran.

Where step a) of the first aspect is conducted in the present of a nitrogen base, the organic solvent is most preferably a halogenated solvent or an amide.

The reaction is typically conducted at a suitable temperature, e.g from about −5° C. to about 40° C. Preferably, the reaction temperature is about 25° C. to about 30° C. The reaction may be allowed to stir for a period of time from about 15 mins to about 16 h and preferably from about 30 mins to about −60 mins.

The resultant organic layer containing protected phosphoramidate of Formula II can be processed directly in the same reaction vessel to form gemcitabine-[phenyl(benzoxy-L-Alaninyl)] phosphate of Formula I. Alternatively, the solvent from the organic layer may be concentrated to obtain a crude product residue by any method known in the art, at the end of the reaction, for example distillation, evaporation, rotational drying (such as with the Buchi rotary evaporator), freeze drying, fluidized bed drying, flash drying, spin flash drying, Preferably the solvent is removed by distillation under vacuum.

The processes of the invention may also involve deprotection of the hydroxy and amino protecting groups.

It may be that the deprotecetion step (step b)) is carried out without purifying the product of step a).

Where a protecting group is acid sensitive, e.g. trityl, C(O)OtBu, MOM, MEM, 2,4-dimethoxybenzyl, 2,3-dimethoxybenzyl, the deprotection step can be conducted using a suitable acid. The acid may be a Bronsted acid (e.g. TFA, phosphoric acid, HCl, or formic acid) or a Lewis acid (e.g. $ZnBr_2$, $CeCl_3$). Lewis acids (e.g. $ZnBr_2$) are less preferred. HCl is likewise less preferred. Preferably, the acid is TFA.

Where a protecting group is base sensitive, e.g. acetyl, benzoyl, the deprotection step can be conducted using a suitable base, e.g. aqueous $NH_3$ or aqueous NaOH. Base sensitive groups may be less preferred.

Where a protecting group is a silyl group (e.g. triethylsilyl or t-butyldimethylsilyl, the deprotection step can be conducted using a suitable acid (e,g, TFA) or using a suitable fluorine source (e.g. tetrabutylammonium fluoride, fluorosilicic acid, HF).

Where a protecting group is a benzyl group or a C(O)Obenzyl group, the deprotection step can be conducted using $H_2$ and a suitable catalyst (e.g. Pd/C). Such protecting groups may be less preferred.

Where a protecting group is a 4-methoxy benzyl, 2,3-dimethoxybenzyl, 2,4-dimethoxybenzyl or C(O)O-(4-methoxybenzyl) the deprotection step can be performed using a suitable oxidizing agent (e.g. meta-chloroperbenzoic acid).

Where a protecting group is —C(O)—O-allyl, the deprotection step can be performed using $(PPh_3)_4Pd$.

Where a protecting group is —C(O)—O—$CH_2$-fluorenyl, the deprotection step can be performed using piperidine.

Where $P^1$ is C(O)OtBu, the deprotection may be achieved using a $C_1$-$C_4$-alcohol and/or water. Where $P^1$ is C(O)OtBu, the deprotection may be achieved using a mixture of a $C_1$-$C_4$-alcohol and water. The deprotection may be achieved using a mixture of isopropyl alcohol (IPA) and water.

The deprotection step may be conducted in an organic solvent or a mixture thereof. Exemplary organic solvents include, but are not limited to halogenated solvents (e.g. dichloromethane, chloroform, dichloroethane); alcohols (e.g. methanol, ethanol, isopropanol) and ethers (e.g. tetrahydrofuran, diethyl ether).

Where the deprotection step is carried out in the presence of an acid (e.g. TFA, the organic solvent is preferably a halogenated solvent, e.g. dichloromethane.

The deprotection reaction may be carried out at a temperature in the range of, for example −10° C. to about 30° C., e.g. to about 10° C. A convenient temperature to carry out the reaction is −5° C. to 5° C. The reaction may be allowed to stir for a period of time from about 15 mins to about 16 hours and preferably from about 1 hour to about 4 hours, and more preferably from about 2 hours to about 3 hours.

Where step b) is achieved using a $C_1$-$C_4$-alcohol and/or water (e.g. a mixture of isopropyl alcohol (IPA) and water), the reaction mixture may be heated, e.g. to a temperature from 30° C. to 90° C. or to a temperature from 60° C. to 85° C.

Where, the deprotection is performed in the presence of an acid (e.g. TFA), isolation of the product obtained after the deprotection is typically done by quenching the excess acid used in deprotection step and extracting the product with a water immiscible organic solvent and recovering the product by evaporation of the organic solvent.

Examples of water immiscible organic solvents useful in extraction include esters such as ethyl acetate, methyl acetate, isopropyl acetate and the like; chlorinated solvents such as dichloromethane, chloroform and the like; aromatic hydrocarbon solvents such as toluene, xylene and the like; preferably ethyl acetate.

It may be that $P^1$ and $P^2$ are both C(O)OtBu groups and $P^3$ is hydrogen, step a) is carried out in the presence of tBuMgCl (e.g. in THF), and step b) is carried out using TFA (e.g. in DCM).

It may be that $P^1$ is a C(O)OtBu group, $P^2$ and $P^3$ area each hydrogen, step a) is carried out in the presence of tBuMgCl (e.g. in THF). It may be that step b) is carried out without isolating the product of step a), e.g. by adding a mixture of IPA and water to the step a) reaction mixture once the reaction of step a) has finished.

In certain embodiments, it may still be desirable to purify the gemcitabine-[phenyl(benzoxy-L-alaninyl)] phosphate obtained from the process of the first aspect of the invention. Likewise, it may still be desirable to purify the compound of formula II obtained from the process of the second aspect of the invention. Methods of purification are well known to those skilled in the art and include chromatography (e.g. column chromatography), recrystallisation and distillation. In other embodiments, no purification is necessary.

The following abbreviations are used throughout this specification:

DCM—dichloromethane DIPE—diisopropylether
DMF—N,N-dimethylformamide DMSO—dimethylsulfoxide
IPA—isopropyl alcohol MTBE—methyl-t-butylether
NMP—N-methylpyrroldinone TBDMS—tert-butyldimethylsilyl
TEA—triethylamine TFA—trifluoroacetic acid
THF—tetrahydrofuran

EXAMPLES

The present invention is further illustrated by the following examples, which are provided by way of illustration only and should not be construed to limit the scope of the invention.

Example 1

Preparation of Diastereoisomeric Mixture of 2-[(2,3,4,5,6-pentafluorophenoxy)-phenoxy-phosphoryl amino] propionic acid benzyl ester (Formula IIa)

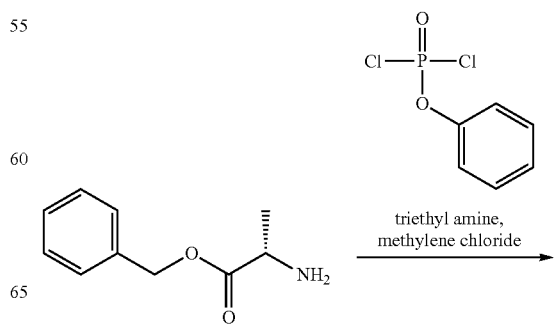

23

-continued

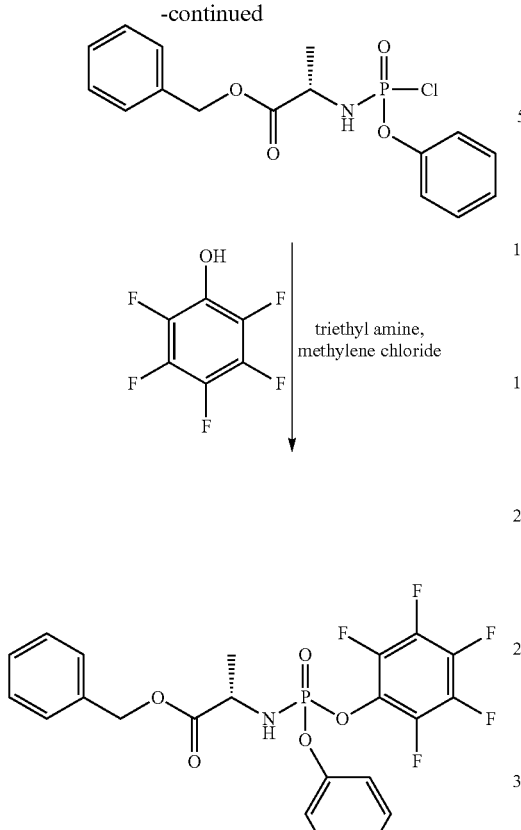

Formula IIa (Sp and Rp mixture)

To a stirred mixture of L-alanine benzyl ester hydrochloride (100 gms) in methylene chloride (1 lit) was added phenyl dichlorophosphate (77 ml) at 25-35° C. and the resulting mixture was cooled to −70° C. to −78° C., added triethyl amine (130.5 ml) and stirred for 1 hrs at same temperature. Reaction mass temperature was raised to 25-35° C. and allowed to stir for 2 hrs. After reaction completion, concentrated the reaction mass under vacuum at below 35° C. to obtain residue. To the obtained residue was added diisopropyl ether (2 lit) at 25-35° C. and stirred for 30 min at same temperature. Filtered the reaction mass and washed with diisopropyl ether (500 ml) followed by concentrating the filtrate under vacuum at below 35° C. to obtain phenyl-(benzoxy-L-alaninyl)-phosphorochloridate. The obtained compound was dissolved in methylene chloride (1 lit) at 25-35° C. and cooled to −5° C. to −10° C. To the reaction mass Pentafluorophenol (85.5 gms), triethyl amine (65.2 ml) was added at same temperature and stirred for 2 hrs. After reaction completion, concentrated the reaction mass under vacuum at below 35° C. and charged ethyl acetate (1 lit) at 25-35° C. and stirred for 30 min at same temperature. Filtered the solids and washed with ethyl acetate (1 lit). To the filtrate was given water (1 lit), 10% sodium carbonate (2×1 lit), brine (1 lit) washings and dried the organic layer with anhydrous sodium sulphate, concentrated under vacuum at 35-45° C. to obtain diastereoisomeric mixture of title compound as a white colored semi solid.

Yield: 210 gms

Chiral Purity by HPLC (% area): 33.74:66.26% ($R_P$: $S_P$)

24

Example 2

Separation of $S_p$-diastereoisomer of 2-[(2,3,4,5,6-pentafluorophenoxy)-phenoxy-phosphoryl amino] propionic acid benzyl ester (Formula IIa)

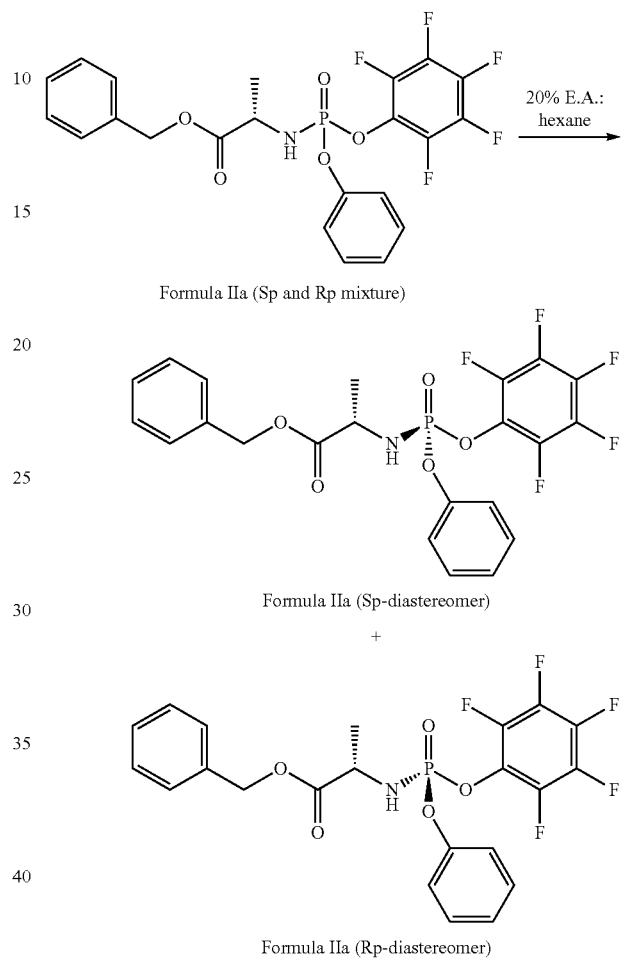

To the above obtained diastereoisomeric mixture of Formula IIa ($R_P$: $S_P$–33.74:66.26%) was charged 20% ethyl acetate in hexane (1.2 lit) at 25-35° C. and stirred for 1 hrs. Filtered the solids and washed with 20% ethyl acetate in hexane (300 ml) to obtain a mixture of compound of Formula IIa.

Yield: 112 gms

Chiral Purity by HPLC (% area): 22.13:77.87% ($R_P$: $S_P$)

Filtrate was concentrated under vacuum to obtain a diastereoisomeric mixture of Formula IIa (75 gm; $R_P$: $S_P$–65.43: 34.57%).

To the above obtained diastereoisomeric mixture of Formula IIa ($R_P$: $S_P$–22.13:77.87%) was charged 20% ethyl acetate in hexane (1.2 lit) at 25-35° C. and stirred for 1 hrs. Filtered the solids and washed with 20% ethyl acetate in hexane (300 ml) to obtain a pure $S_p$-diastereoisomer of compound of Formula IIa.

Yield: 80 gms

Chiral Purity by HPLC (% area): 0.20:99.80% ($R_P$: $S_P$)

$^1$H NMR (300 MHz, DMSO-$d_6$): 7.18-7.41 (m, 10H), 6.91-6.99 (d, 1H), 5.10 (s, 2H), 4.01-4.11 (m, 1H), 1.30-1.32 (d, 3H)

ESI-MS (m/z): 524 (M+1)

Filtrate was concentrated under vacuum to obtain a diastereoisomeric mixture of Formula IIa (28 gm; $R_P$: $S_P$–80.77: 19.23%).

Example 3

Isomerization of 2-[(2,3,4,5,6-pentafluorophenoxy)-phenoxy-phosphoryl amino] propionic acid benzyl ester (Formula IIa)

To a stirred solution of above obtained 2-[(2,3,4,5,6-pentafluorophenoxy)-phenoxy-phosphoryl amino] propionic acid benzyl ester of Formula IIa (75 gms; $R_P$: $S_P$–65.43:34.57%) in 20% ethyl acetate in hexane (1.1 lit), triethyl amine (7.5 ml) was added at 25-35° C. and stirred for 6 hrs at same temperature. After reaction completion, reaction mass was quenched in to a water (750 ml) and extracted with ethyl acetate (750 ml). Organic layer was dried with anhydrous sodium sulphate and concentrated under vacuum to afford title compound as a solid.

Yield: 45 gms
Chiral Purity by HPLC (% area): 91.29: 8.71% ($S_P$: $R_P$)

To the above obtained $R_p$ and $S_p$-diastereoisomeric mixture of 2-[(2,3,4,5,6-pentafluorophenoxy)-phenoxy-phosphoryl amino] propionic acid benzyl ester of Formula IIa (45 gms; $R_P$: $S_P$–8.71:91.29%) was slurred in 20% ethyl acetate in hexane (1.1 lit) at 25-30° C. and stirred for 1 hr at same temperature. Filtered the solid and washed with 20% ethyl acetate in hexane (225 ml) to obtain $S_p$-diastereoisomer of the title compound as a solid.

Yield: 19 gms
Chiral Purity by HPLC (% area): 99.92: 0.08% ($S_P$: $R_p$)

Example 4

Preparation of $S_p$-diastereoisomer of NUC-1031 (using $S_p$-diastereoisomer of Formula IIa)

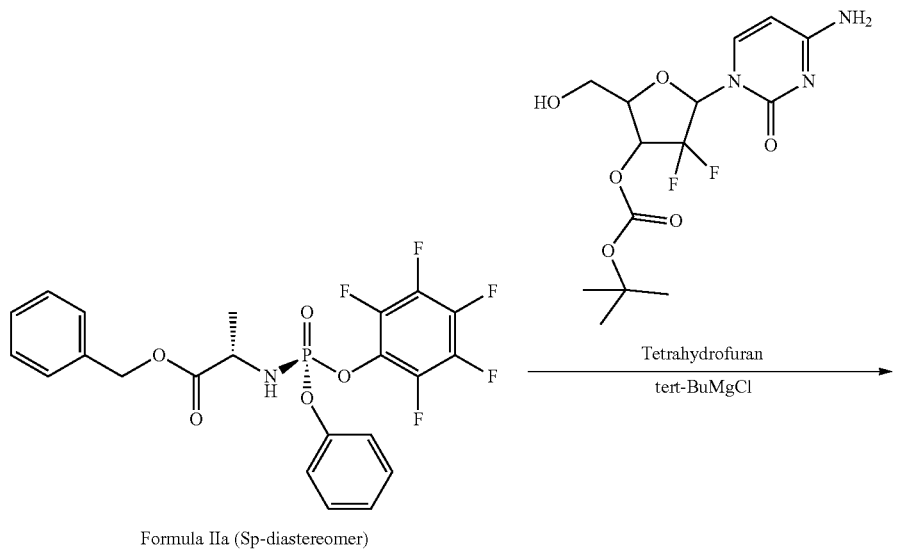

Formula IIa (Sp-diastereomer)

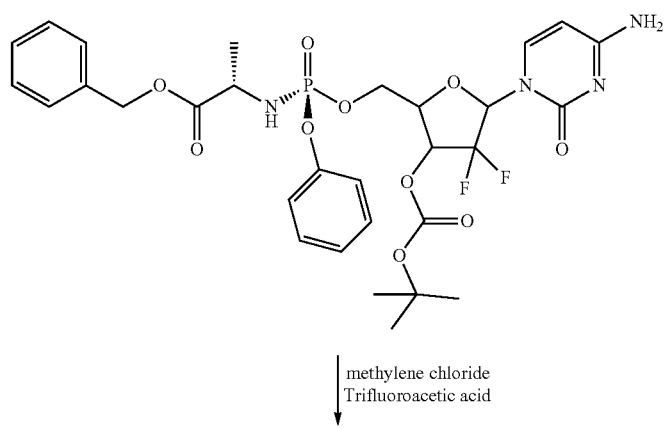

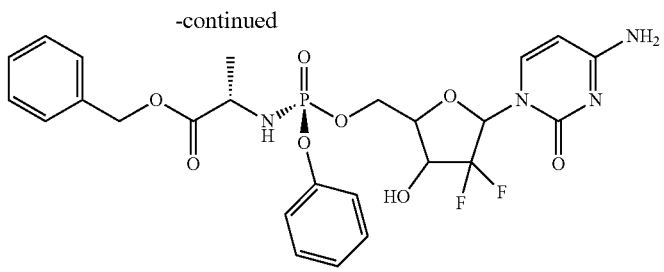

Formula I (Sp-diastereomer)

To a stirred mixture of 3'-O-(tert-butoxycarbonyl) gem-citabine (5 gms) in tetrahydrofuran (75 ml), was added tert-butyl magnesium chloride (15.2 ml of 2.0 M in tetrahydrofuran) and $S_p$-diastereoisomer of 2-[(2,3,4,5,6-pentafluorophenoxy)-phenoxy-phosphoryl amino] propionic acid benzyl ester of Formula IIa (8.3 gms diluted in 50 ml of tetrahydrofuran)) at 0° C. to −5° C. and temperatures was raised to 25-30° C. and stirred for 30 min at same temperature. After reaction completion, reaction mass was quenched in to 0.5 N hydrochloric acid (50 ml) and extracted with ethyl acetate (2×75 ml). To the organic layer was given 10% sodium carbonate (2×50 ml), brine solution (50 ml) washings sequentially. The organic layer separated, dried over sodium sulfate and concentrated under vacuum to obtain a residue.

The obtained residue was taken up in methylene chloride (50 ml) and added trifluoro acetic acid (18.5 ml) at 0° C. to 5° C. Maintained the reaction mass at 25-35° C. for 2 hrs and quenched in to 20% sodium carbonate solution (125 ml). Extracted with ethyl acetate (165 ml), dried the organic layer over sodium sulfate and evaporated under vacuum at 40-45° C. The obtained residue was slurried in 50% ethyl acetate in heptane (150 ml) mixture to obtain the title compound.

Yield: 4.8 gms

Chiral Purity by HPLC (% area): 99.4% ($S_P$-diastereoisomer)

Example 5

Preparation of Diastereoisomeric Mixture of 2-[(4-nitrophenoxy)-phenoxy-phosphorylamino] propionic acid benzyl ester of Formula IIb

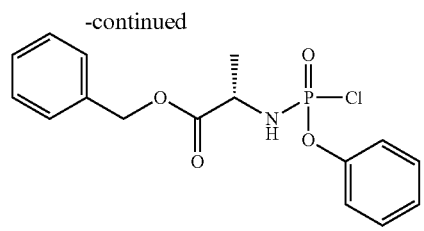

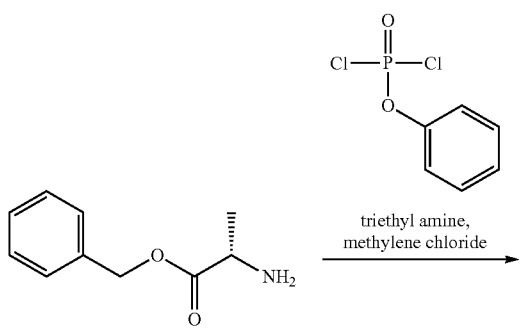

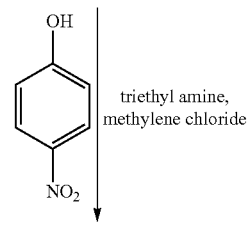

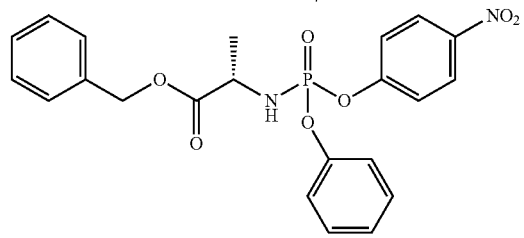

Formula IIb (Sp and Rp mixture)

To a stirred mixture of L-alanine benzyl ester hydrochloride (50 gms) in methylene chloride (500 ml) was added phenyl dichlorophosphate (54 gms) at 25-35° C. and the resulting mixture was cooled to −70° C. to −78° C., added triethyl amine (65.2 ml) and stirred for 1 hrs at same temperature. Reaction mass temperature was raised to 25-35° C. and allowed to stir for 2 hrs. After reaction completion, concentrated the reaction mass under vacuum at below 35° C. to obtain residue. To the obtained residue was added diisopropyl ether (1 litre) at 25-35° C. and stirred for 30 min at same temperature. Filtered the reaction mass and washed with diisopropyl ether (250 ml) followed by concentrating the filtrate under vacuum at below 35° C. to obtain phenyl-(benzoxy-L-alaninyl)-phosphorochloridate. The obtained compound was dissolved in methylene chloride (500 ml) at 25-35° C. and cooled to −5° C. to −10° C. To the reaction mass pentafluorophenol (27.5 gms), triethyl amine (65.2 ml) was added at same temperature and stirred for 2 hrs. After reaction completion, concentrated the reaction mass under vacuum at below 35° C. and charged ethyl acetate (500 ml) at 25-35° C. and stirred for 30 min at same temperature. Filtered the solids and washed with ethyl acetate (500 ml). To the filtrate was given water (500 ml), 10% sodium carbonate (2×500 ml), brine (500 ml) washings and dried the organic layer with anhydrous sodium sulphate, concentrated under vacuum at 35-40° C. to obtain diastereoisomeric mixture of title compound as a thick oily liquid.

Yield: 90 gms

Chiral Purity by HPLC (% area): 45.6: 54.94% ($R_P$: $S_P$)

The above obtained diastereoisomeric mixture of 2-[(4-nitrophenoxy)-phenoxy-phosphorylamino] propionic acid benzyl ester of Formula IIb (40 gms; $R_p$: $S_p$–45.6: 54.94%) was separated in to pure $S_p$ and $R_p$ diastereoisomers by preparative HPLC and concentrated the pure fractions under vacuum to obtain $S_p$ and $R_p$ diastereoisomers separately.

Yield: $S_p$-diastereoisomer: 8 gms,
$^1$H NMR (300 MHz, CDCl$_3$): –8.15-8.19 (d, 2H), 7.15-8.37 (m, 12H), 5.12 (s, 2H), 4.02-4.24 (m, 2H), 1.39-1.42 (d, 3H)
ESI-MS (m/z): –479 (M+Na)
$R_p$-diastereoisomer: 6 gms,
$^1$H NMR (300 MHz, CDCl$_3$): –8.08-8.13 (d, 2H), 7.15-7.34 (m, 12H), 5.10 (s, 2H), 4.48-4.56 (m, 1H), 4.11-4.20 (m, 1H), 1.39-1.41 (d, 3H)
ESI-MS (m/z): –457 (M+1)$^+$
$S_p$ & $R_p$-diastereoisomer mixture: 20 gms Example 6

Preparation of $S_p$-diastereoisomer of NUC-1031 (using $S_p$-diastereoisomer of Formula IIb)

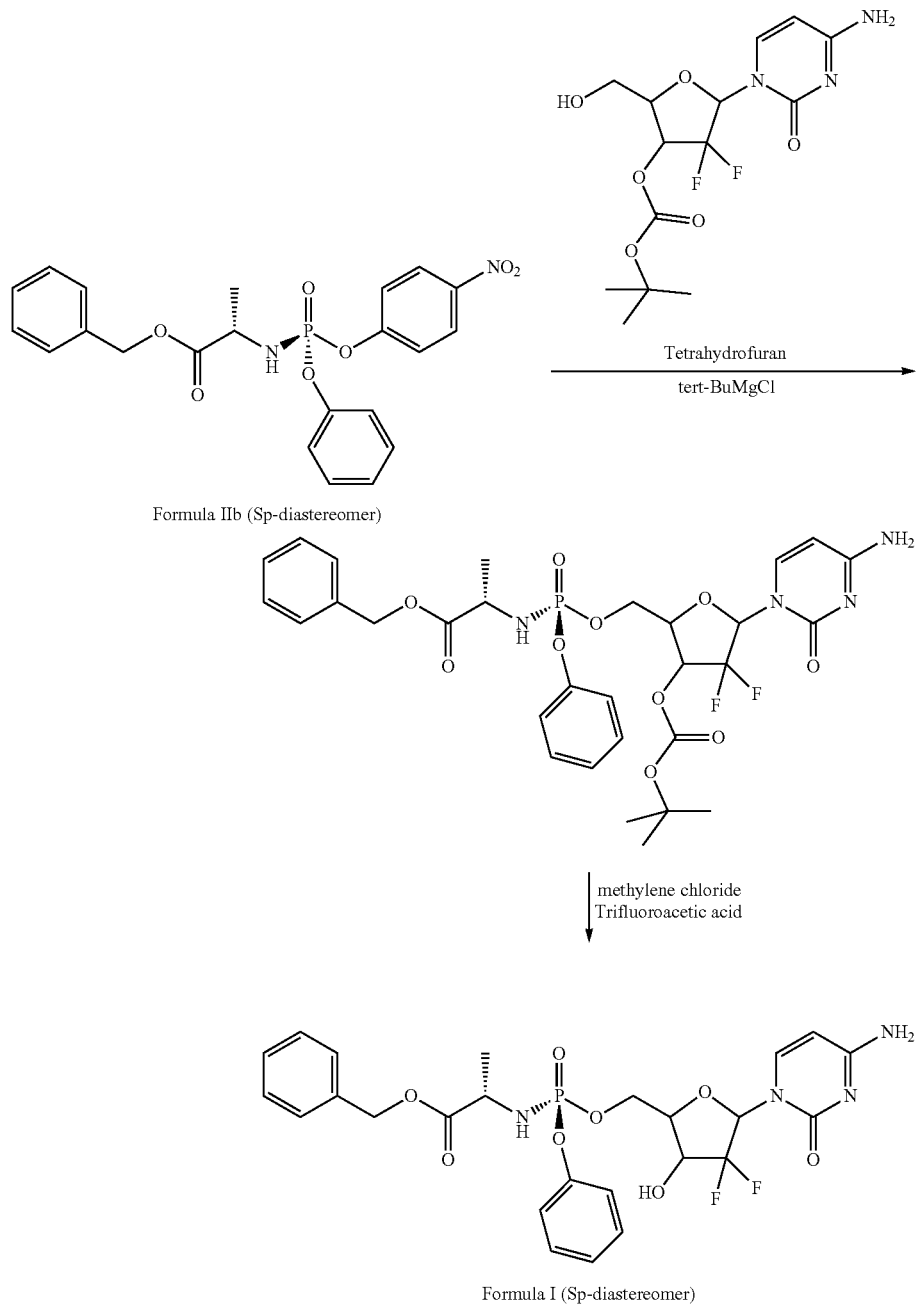

To a stirred mixture of 3'-O-(tert-butoxycarbonyl) gemcitabine (2 gms) in tetrahydrofuran (30 ml), was added N-methyl pyridine (2 ml), tert-butyl magnesium chloride (5.5 ml of 2.0 M in tetrahydrofuran) and $S_p$-diastereoisomer of 2-[(4-nitrophenoxy)-phenoxy-phosphorylamino] propionic acid benzyl ester of Formula IIb (4 gms diluted in 20 ml of tetrahydrofuran) at 0° C. to −5° C. and temperatures was raised to 25-30° C. and stirred for 30 min at same temperature. After reaction completion, reaction mass was quenched in to 0.5 N hydrochloric acid (20 ml) and extracted with ethyl acetate (2×30 ml). To the organic layer was given 10% sodium carbonate (2×20 ml), brine solution (20 ml) washings sequentially. The organic layer separated, dried over sodium sulfate and concentrated under vacuum to obtain a residue.

The obtained residue was taken up in methylene chloride (20 ml) and added trifluoro acetic acid (7.4 ml) at 0° C. to 5° C. Maintained the reaction mass at 25-35° C. for 2 hrs and quenched in to 20% sodium carbonate solution (30 ml). Extracted with ethyl acetate (66 ml), dried the organic layer over sodium sulfate and evaporated under vacuum at 40-45° C. The obtained residue (3 gms; $S_p$-85.98%) was purified by column chromatography method by eluting with 2-10% isopropanol in methylene chloride mixture. The product containing fractions were collected and concentrated under vacuum to obtain a title compound as a solid.

Yield: 1.1 gms

Chiral Purity by HPLC (% area): 97.88: 0.48% ($S_p$: $R_p$)

Example 7

Preparation of $R_p$-diastereoisomer of gemcitabine-[phenyl (benzoxy-L-alaninyl)] phosphate of Formula I (using $R_p$-diastereoisomer of Formula IIb)

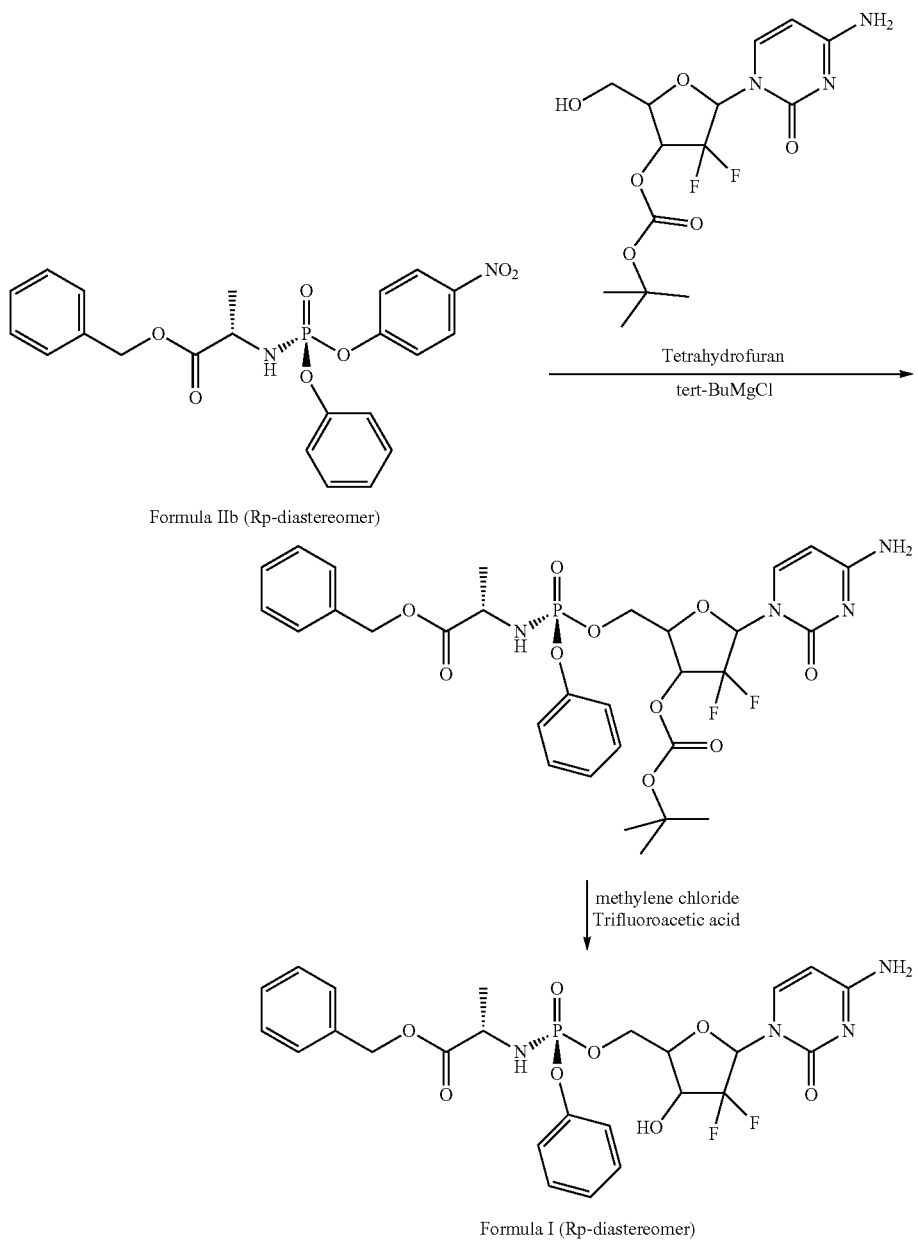

Formula IIb (Rp-diastereomer)

methylene chloride
Trifluoroacetic acid

Formula I (Rp-diastereomer)

To a stirred mixture of 3'-O-(tert-butoxycarbonyl) gemcitabine (2 gms) in tetrahydrofuran (30 ml), was added N-methyl pyridine (2 ml), tert-butyl magnesium chloride (5.5 ml of 2.0 M in tetrahydrofuran) and $R_p$-diastereoisomer of 2-[(4-nitrophenoxy)-phenoxy-phosphorylamino] propionic acid benzyl ester of Formula IIb (4 gms diluted in 20 ml of tetrahydrofuran) at 0° C. to −5° C. and temperatures was raised to 25-30° C. and stirred for 30 min at same temperature. After reaction completion, reaction mass was quenched in to 0.5 N hydrochloric acid (20 ml) and extracted with ethyl acetate (2×30 ml). To the organic layer was given 10% sodium carbonate (2×20 ml), brine solution (20 ml) washings sequentially. The organic layer separated, dried over sodium sulfate and concentrated under vacuum to obtain a residue.

The obtained residue was taken up in methylene chloride (20 ml) and added trifluoro acetic acid (7.4 ml) at 0° C. to 5° C. Maintained the reaction mass at 25-35° C. for 2 hrs and quenched in to 20% sodium carbonate solution (30 ml). Extracted with ethyl acetate (66 ml), dried the organic layer over sodium sulfate and evaporated under vacuum at 40-45° C. The obtained residue (2.9 gms; $R_p$-84.05%) was purified by column chromatography method by eluting with 2-10% isopropanol in methylene chloride mixture. The product containing fractions were collected and concentrated under vacuum to obtain a title compound as a solid.

Yield: 1.4 gms

Chiral Purity by HPLC (% area): 97.99: 0.86% ($R_p$: $S_p$)

Example 8

Preparation of $S_p$-diastereoisomer of gemcitabine-[phenyl (benzoxy-L-alaninyl)] phosphate of Formula I (using isomerised $S_p$-diastereoisomer of Formula IIa from example-3)

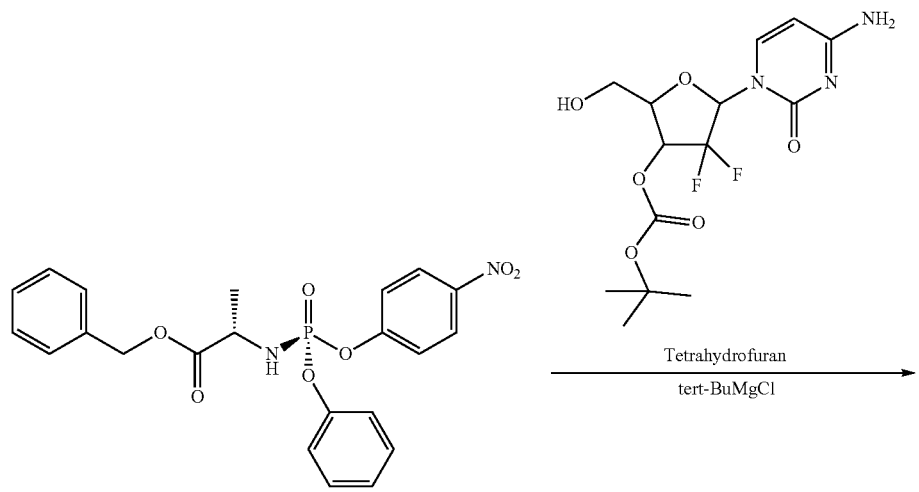

Formula IIb (Sp-diastereomer)

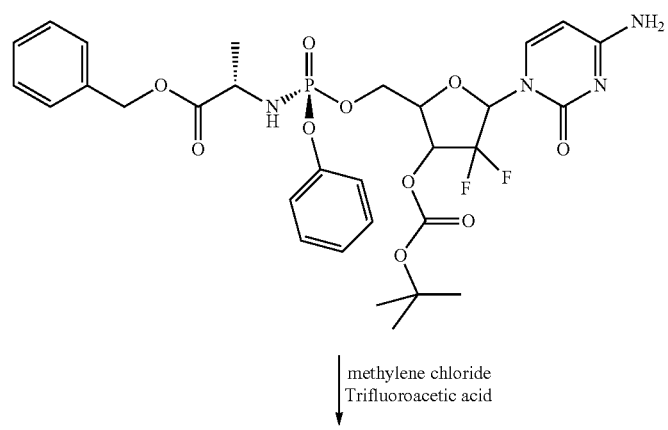

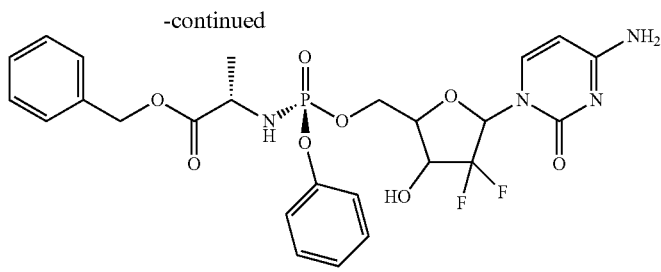

Formula I (Sp-diastereomer)

To a stirred mixture of 3'-O-(tert-butoxycarbonyl) gemcitabine (5 gms) in tetrahydrofuran (75 ml), was added tert-butyl magnesium chloride (15.2 ml of 2.0 M in tetrahydrofuran) and $S_P$-diastereoisomer of 2-[(2,3,4,5,6-pentafluorophenoxy)-phenoxy-phosphoryl amino] propionic acid benzyl ester of Formula IIa (8.3 gms from example-3 (99.92%); diluted in 50 ml of tetrahydrofuran) at 0° C. to −5° C. and temperatures was raised to 25-30° C. and stirred for 30 min at same temperature. After reaction completion, reaction mass was quenched in to 0.5 N hydrochloric acid (50 ml) and extracted with ethyl acetate (2×75 ml). To the organic layer was given 10% sodium carbonate (2×50 ml), brine solution (50 ml) washings sequentially. The organic layer separated, dried over sodium sulfate and concentrated under vacuum to obtain a residue.

The obtained residue was taken up in methylene chloride (50 ml) and added trifluoro acetic acid (18.5 ml) at 0° C. to 5° C. Maintained the reaction mass at 25-35° C. for 2 hrs and quenched in to 20% sodium carbonate solution (125 ml). Extracted with ethyl acetate (165 ml), dried the organic layer over sodium sulfate and evaporated under vacuum at 40-45° C. The obtained residue was slurried in 50% ethyl acetate in heptane (150 ml) mixture to obtain the title compound.

Yield: 4.9 gms

Chiral Purity by HPLC (% area): 99.72% ($S_P$-diastereoisomer)

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

Example 9

Preparation of $S_P$-diastereoisomer of NUC-1031 (using $S_P$-diastereoisomer of Formula IIb) using IPA/water for Deprotection

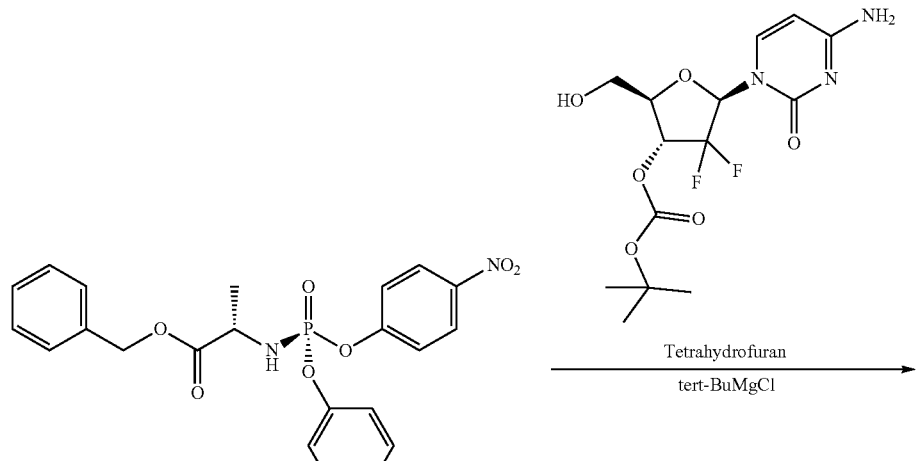

Formula IIb (Sp-diastereomer)

-continued

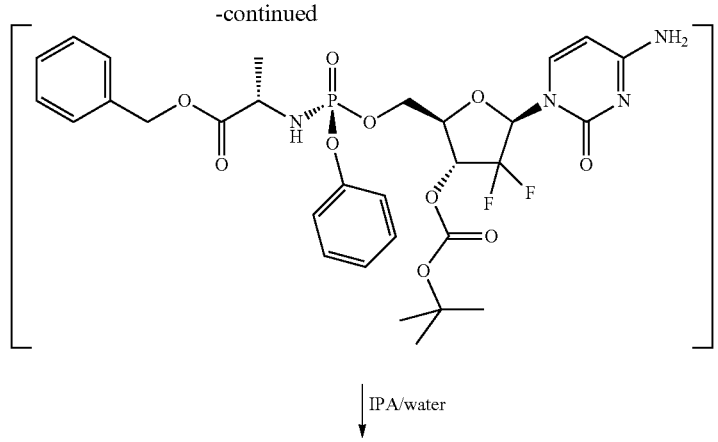

↓ IPA/water

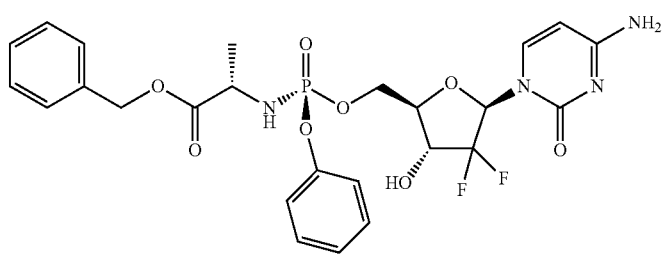

Formula I (Sp-diastereomer)

To a stirred mixture of 3'-O-(tert-butoxycarbonyl) gem-citabine (100 gms) in tetrahydrofuran (1 L), tert-butyl magnesium chloride (292 mL of 2.0 M in tetrahydrofuran) and $S_p$-diastereoisomer of 2-[(4-nitrophenoxy)-phenoxy-phosphorylamino] propionic acid benzyl ester of Formula IIb (166 gms diluted in 700 mL of tetrahydrofuran) at −5° C. to −0° C. and temperatures was raised to 25-30° C. and stirred for 3 h at the same temperature. After reaction completion, reaction mass was quenched in to 0.5 N hydrochloric acid (1 L) and extracted with ethyl acetate. The organic layer was sequentially washed with 10% sodium carbonate, water and brine solution washings sequentially. The organic layer was separated and concentrated under vacuum to obtain a residue. Isopropyl alcohol (IPA; 850 mL) and water (2.5 L) were added to the residue and the mixture was heated to 75° C. for 3 h before more water was added (2.5 L) and the mixture was cooled to 25° C. and filtered. The resultant solid was washed with ethyl acetate and dried. 124 g of product was obtained (78%). Chiral Purity by HPLC (% area): 99.95% ($S_P$-diastereoisomer)

Example 10—Preparation of (Sp)-2-[(2,3,4,5,6-pentafluorophenoxy)-phenoxy-phosphoryl amino] propionic acid benzyl ester (Formula IIa)

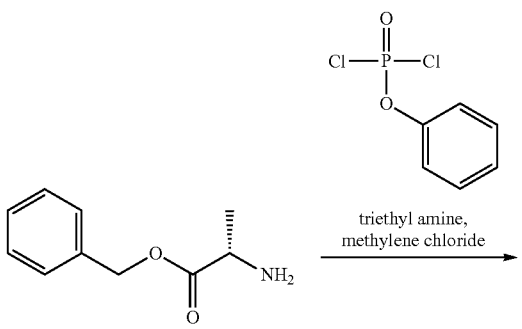

triethyl amine, methylene chloride

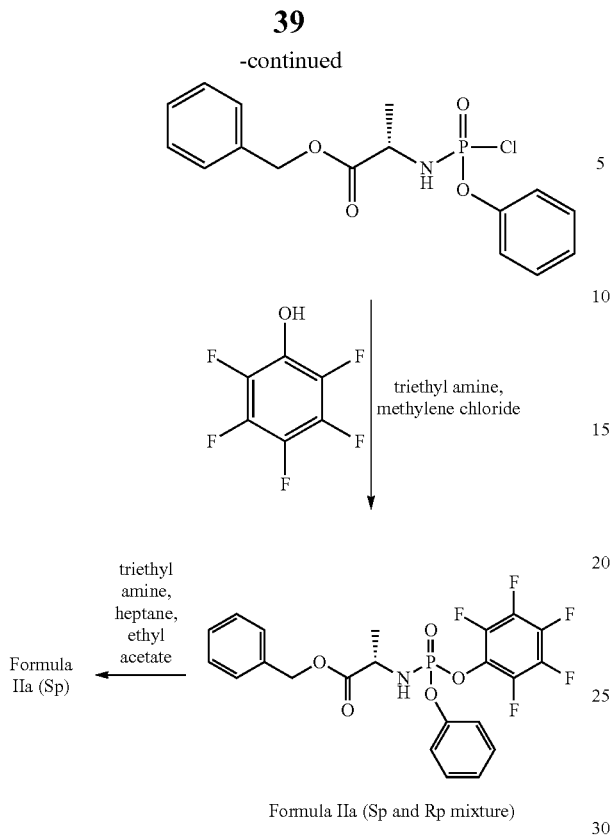

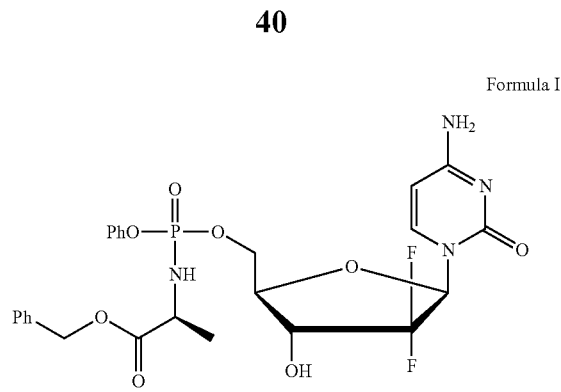

Formula I

To a stirred mixture of L-Alanine Benzyl ester. HCl (100 g) in 1000 mL of methylene dichloride was added phenyl dichlorophosphate (97.8 g) into reaction mass at 30° C. The mixture was cooled to −20° C. and triethylamine (93.8 g) was added slowly, maintaining the temperature at −20° C. The reaction was stirred for 1 h at −20° C., then warmed to 10° C. (10±5) and stirred for a further 1.5 h.

A solution of pentafluorophenol (85.3 g) in 100 mL of methylene dichloride was slowly added at 10° C. followed by trimethylamine (46.8 g) which is added slowly, maintaining the temperature at 10° C. Slowly add 46.9 g of triethylamine into reaction mass at 10° C. (10±5) under nitrogen atmosphere. The mixture was stirred for 2 h at 10° C. before being quenched by slow addition of 0.5 N HCl solution, maintaining the temperature at 10° C. After warming to room temperature the mixture was separated and the organics was washed with a saturated bicarbonate solution, distilled water and brine before being concentrated in vacuo.

The crude mixture was suspended in 1500 mL of 20% ethyl acetate in n-heptane at 25° C. Triethylamine (12.2 g) was added and the mixture was stirred at 25°. The mixture was filtered and the solid dissolved in 2500 mL ethyl acetate which was washed with water and brine and concentrated in vacuo. The solid was suspended in 1200 mL of 20% ethyl acetate in n-heptane, stirred for 45-60 min and filtered. The material was dried under vacuum to provide the desired product. Yields are in the range 40 to 80% and the diastereoisomeric purity is over 99%.

The invention claimed is:

1. A process for the preparation of gemcitabine-[phenyl (benzoxy-L-alaninyl)] phosphate (Formula I) having a diastereoisomeric purity of greater than about 95%:

the process comprising steps a) to d), and optionally step e):

a) suspending or dissolving the (R)-diastereoisomer of a compound of Formula II or a mixture of the (R)- and (S)-diastereoisomers of the compound of Formula II in a solvent (S2);

b) treating the solution or suspension with a base (B2) to obtain the (S)-diastereoisomer having a diastereoisomeric purity of greater than about 95%;

c) isolating the (S)-diastereoisomer of Formula II, having a diastereoisomeric purity of greater than about 95%;

d) reacting the compound of Formula II, having a diastereoisomeric purity of greater than about 95%; wherein $R^1$ represents an electron withdrawing group and a is an integer from 1 to 5, with a compound of Formula III in presence of a base (B1) to provide the (S)-diastereoisomer of a compound of Formula IV having a diastereoisomeric purity of greater than about 95%; wherein $P^1$, $P^2$ and $P^3$ each independently represents hydrogen or a protecting group:

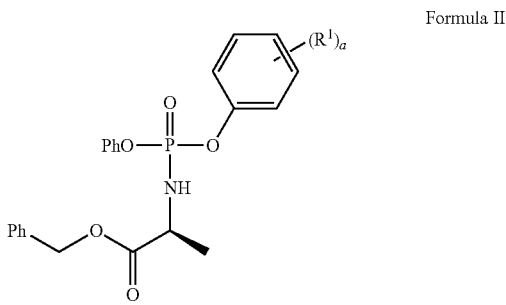

Formula II

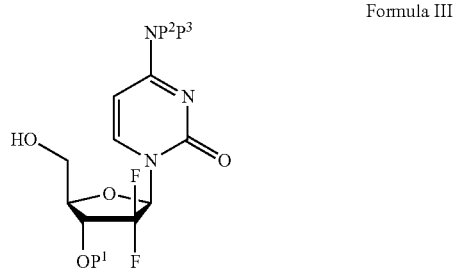

Formula III

Formula IV

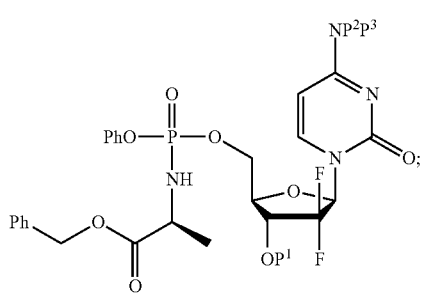

and e) where any one or more of $P^1$, $P^2$ and $P^3$ are protecting groups, optionally removing the protecting groups $P^1$, $P^2$ and $P^3$ from the compound of formula IV to provide gemcitabine-[phenyl (benzoxy-L-alaninyl)] phosphate having a diastereoisomeric purity of greater than about 95%.

2. The process of claim 1, wherein $P^1$ is —C(O)O$C_1$—$C_6$-alkyl or optionally substituted —C(O)OCH$_2$-aryl.

3. The process of claim 2, wherein $P^1$ is —C(O)O$^t$Bu.

4. The process of claim 3, wherein step e) is achieved by reacting the product of step d) with a mixture of a $C_1$-$C_4$-alcohol and water.

5. The process of claim 1, wherein $P^2$ is H.

6. The process of claim 1, wherein $P^3$ is H.

7. The process of claim 1, wherein $B^1$ is a Grignard reagent.

8. The process of claim 7, wherein $B^1$ is $^t$BuMgCl.

9. The process of claim 1, wherein step d) is conducted in an ether solvent.

10. The process of claim 9, wherein step d) is conducted in THF.

11. The process of claim 1, wherein the compound of Formula II is a compound selected from:

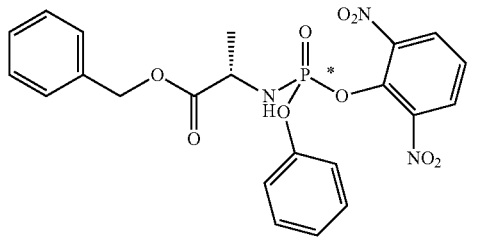

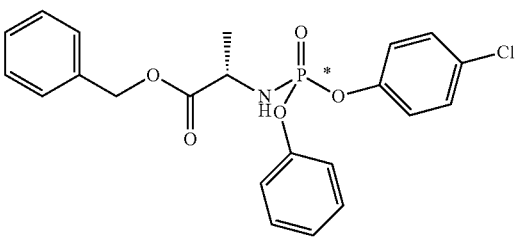

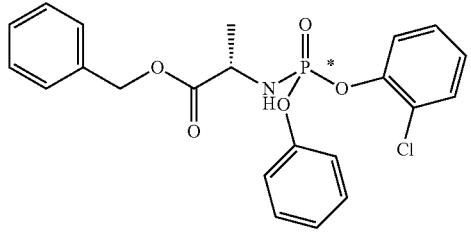

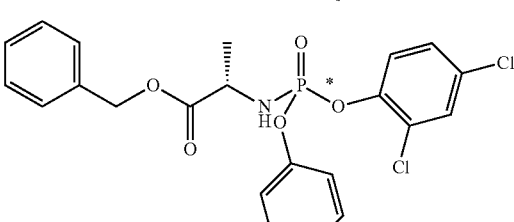

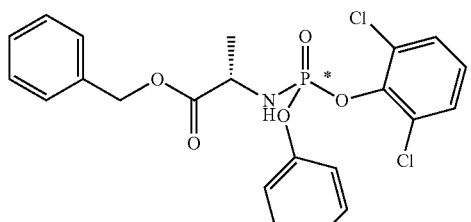

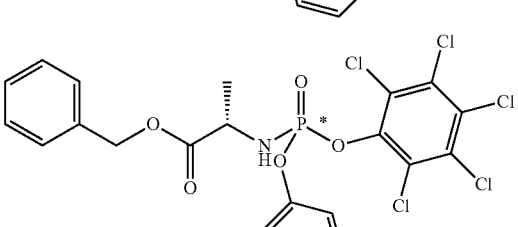

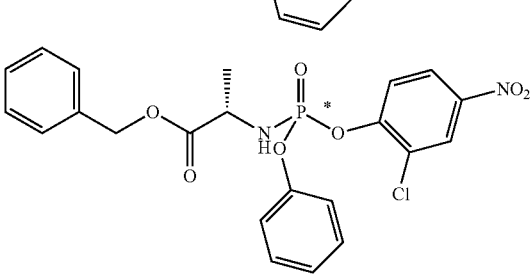

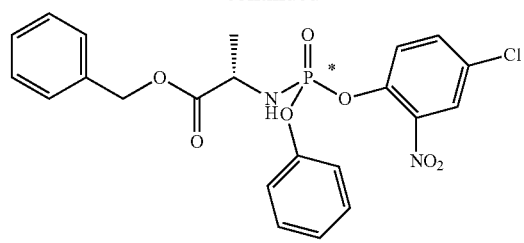
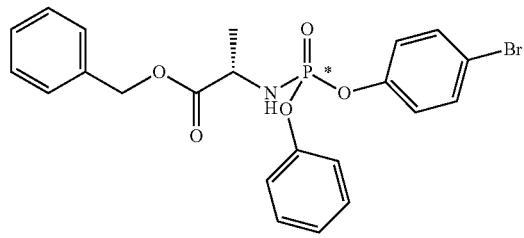
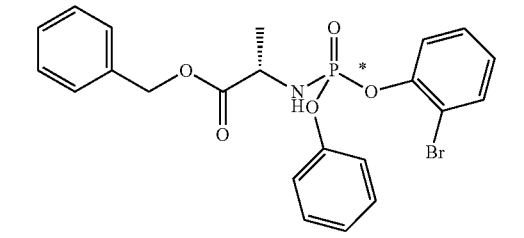
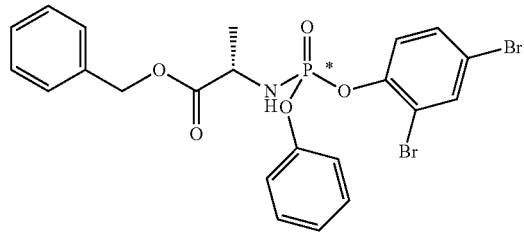
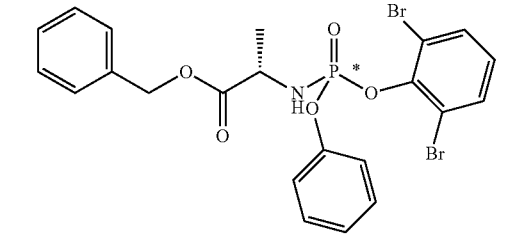
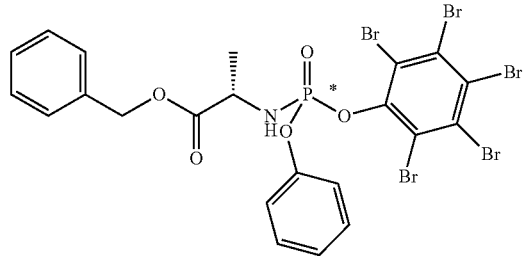
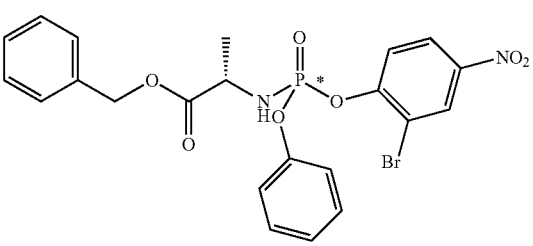
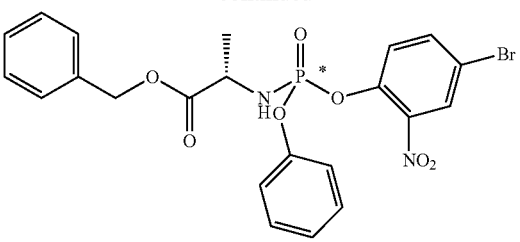
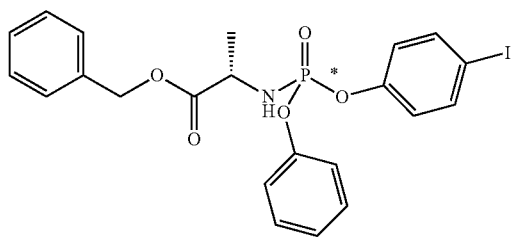
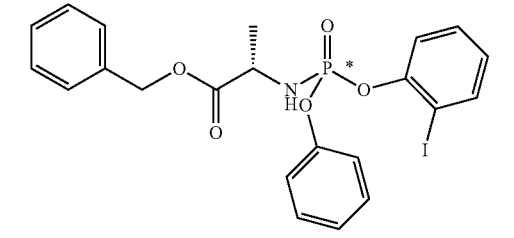
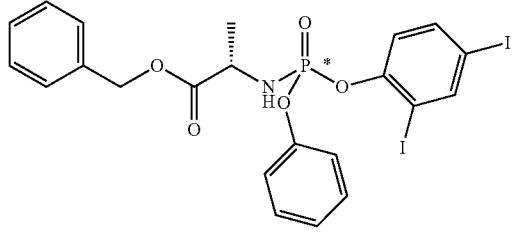
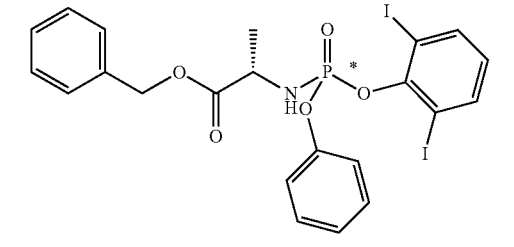
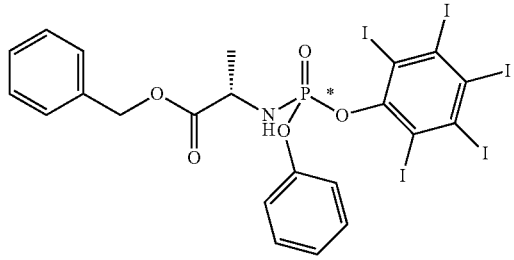
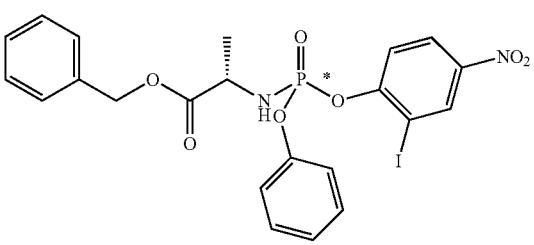

45
-continued
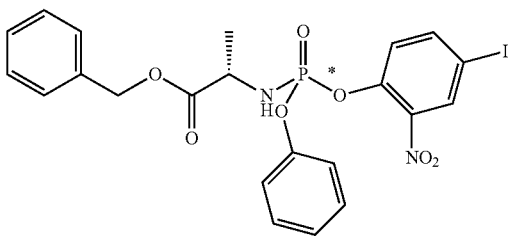
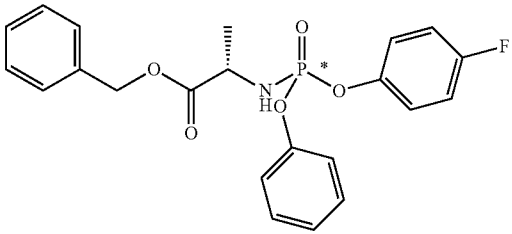
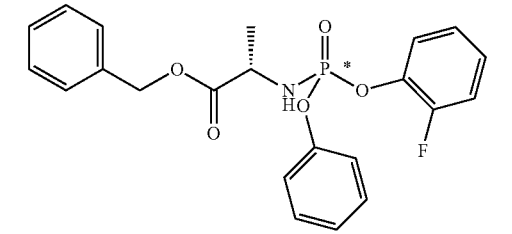
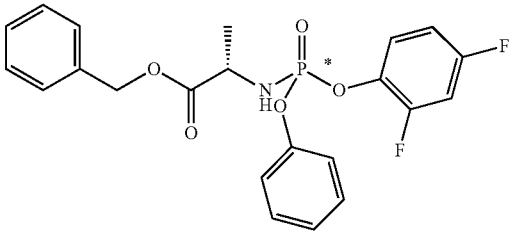
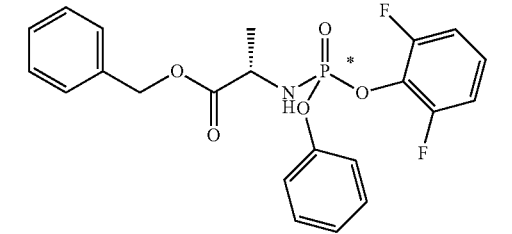
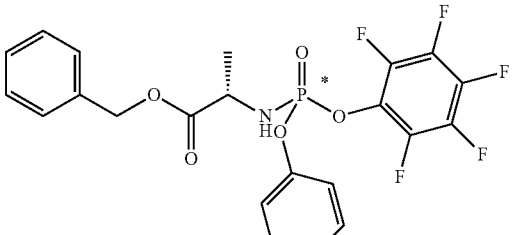
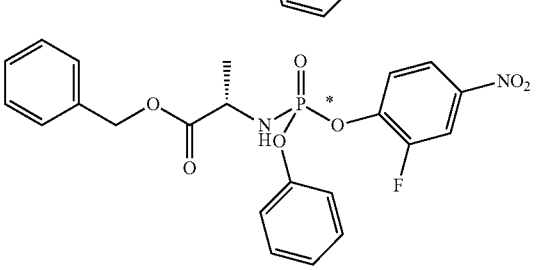
46
-continued
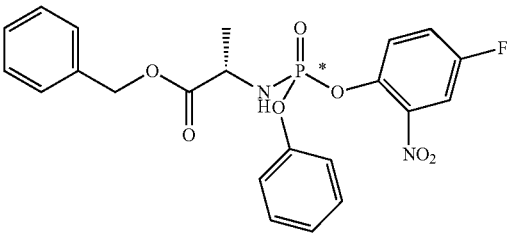
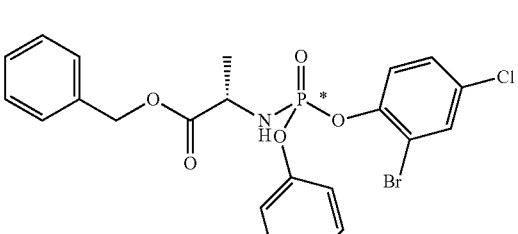
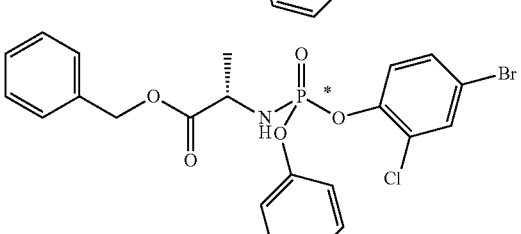
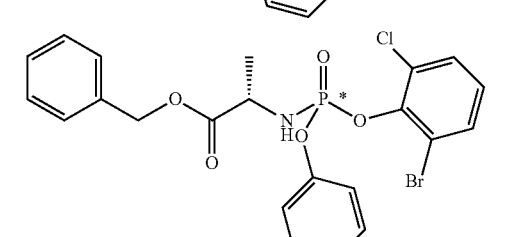
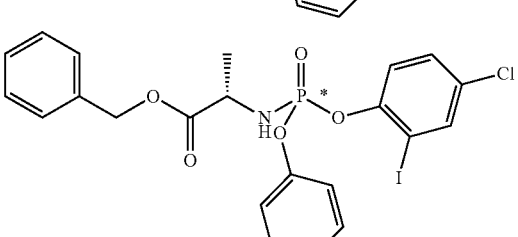
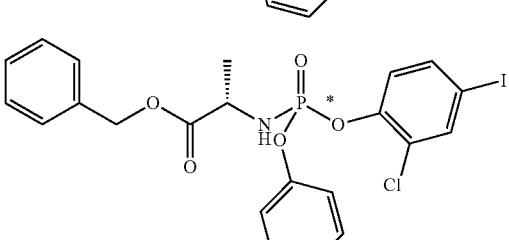
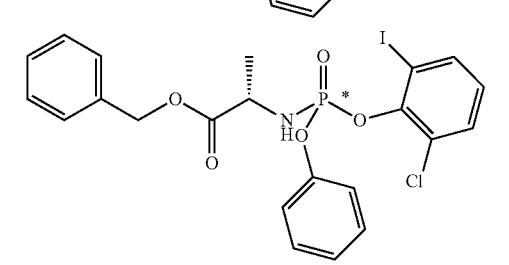

47
-continued
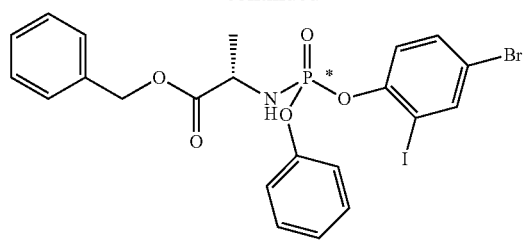
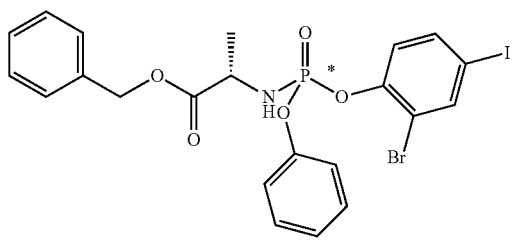
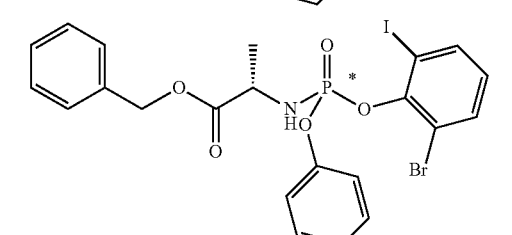
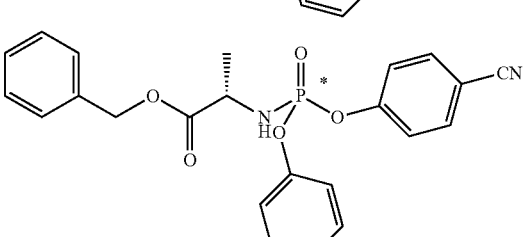
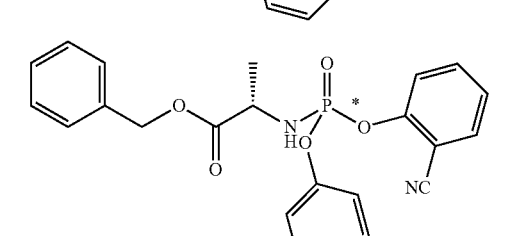
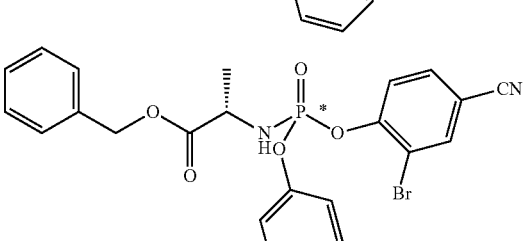
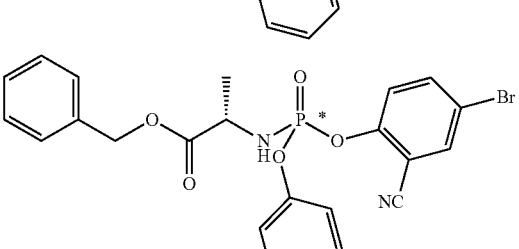
48
-continued
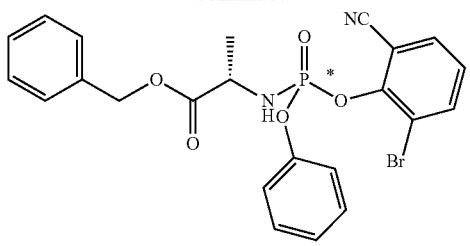
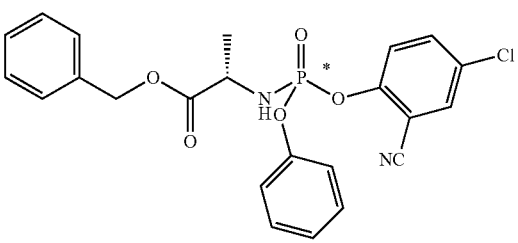
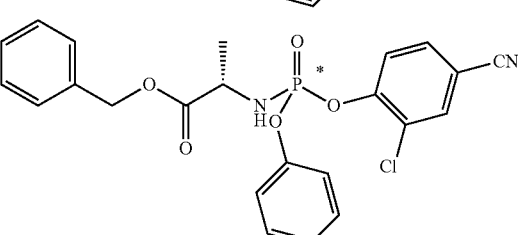
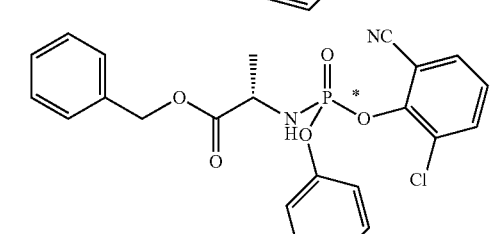
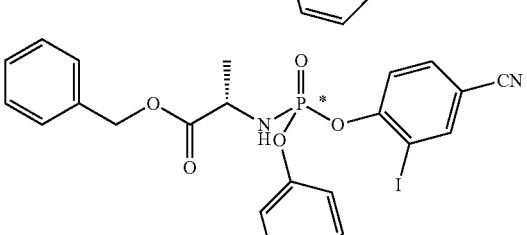
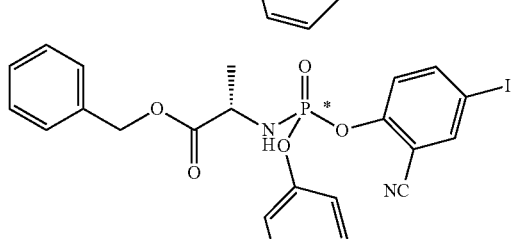
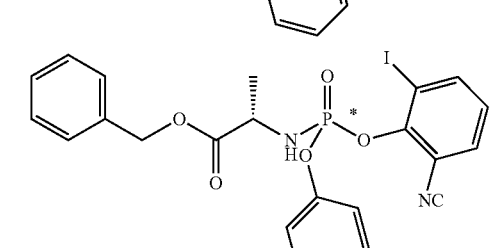

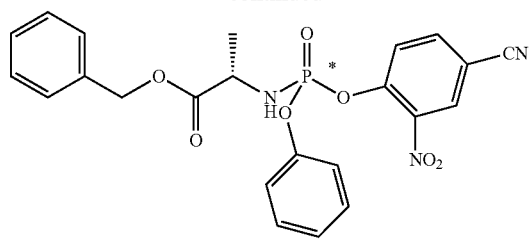
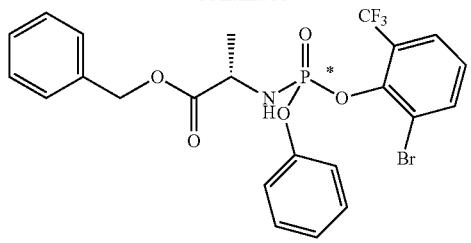
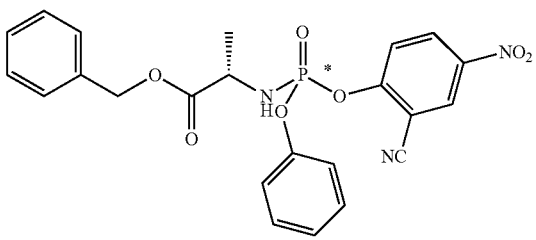
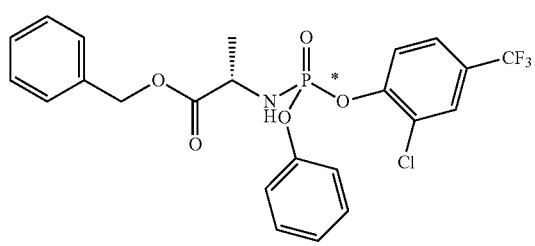
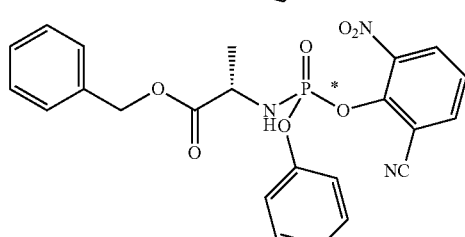
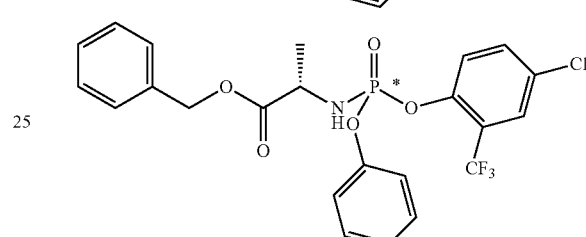
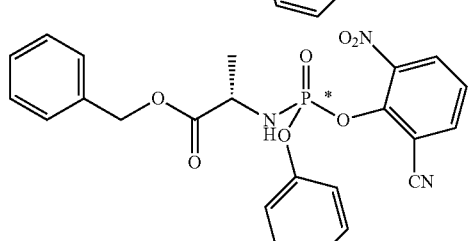
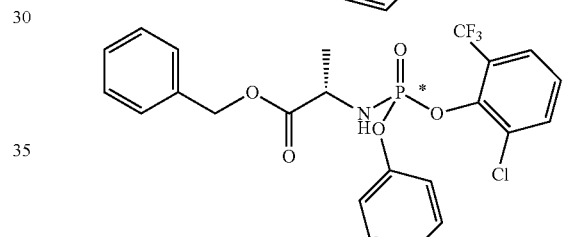
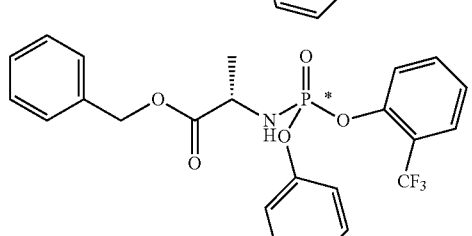
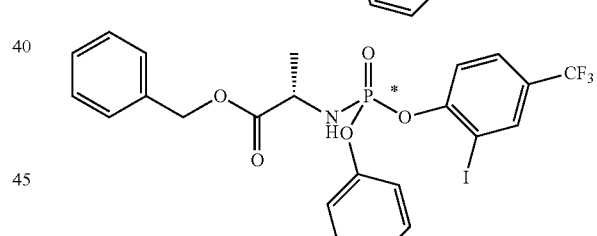
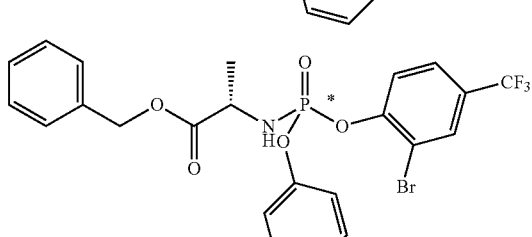
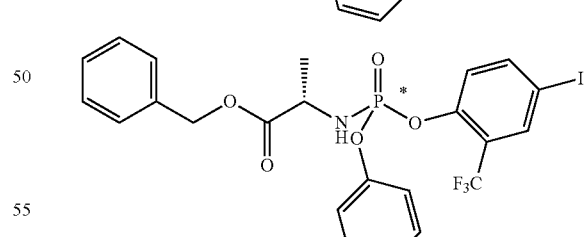
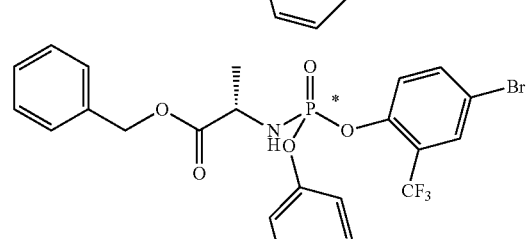
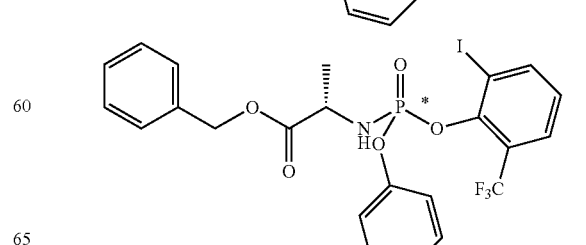

-continued

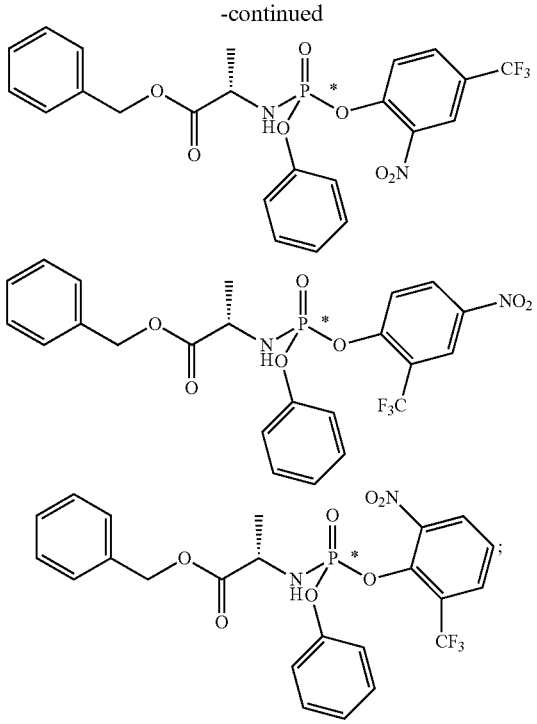

and *represents chiral center.

12. The process of claim 1, wherein the compound of formula II is:

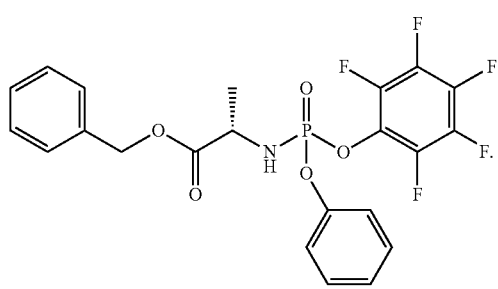 [SMILES: C[C@H](NP(=O)(Oc1ccccc1)Oc1c(F)c(F)c(F)c(F)c1F)C(=O)OCc1ccccc1]

13. The process of claim 1, wherein the compound of formula II is:

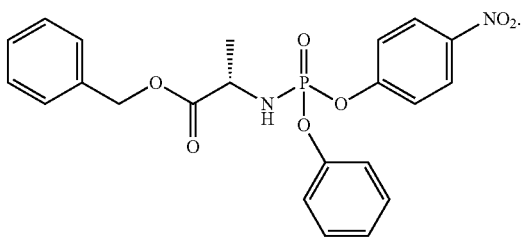 [SMILES: C[C@H](NP(=O)(Oc1ccccc1)Oc1ccc([N+](=O)[O-])cc1)C(=O)OCc1ccccc1]

14. A process for the diastereoisomeric enrichment of a compound of Formula II, comprising the steps of:
 a) suspending or dissolving the (R)-diastereoisomer of the compound of Formula II or a mixture of the (R)- and (S)-diastereoisomers of the compound of Formula II in a solvent (S2),
 b) treating the solution or suspension with a base (B2) to obtain the (S)-diastereoisomer having a diastereoisomeric purity of greater than about 95%, and
 c) isolating the (S)-diastereoisomer of Formula II.

15. The process of claim 14, further comprising
 forming the compound of Formula II as a mixture of the (R)- and (S)-diastereoisomers; and
 wherein step a) comprises suspending or dissolving the mixture of the (R)- and (S)-diastereoisomers of the compound of Formula II in the solvent (S2).

16. The process of claim 1, wherein B2 is a tertiary amine.

17. The process of claim 16, wherein B2 is triethylamine.

18. The process of claim 1, wherein S2 is a hydrocarbon or a mixture comprising a hydrocarbon.

19. The process of claim 18, wherein S2 is hexane or heptane.

20. The process of claim 18 wherein S2 is a mixture of hexane or heptane and a polar organic solvent, and the mixture comprising over 50% by volume hexane or heptane.

21. The process of claim 20, wherein S2 is a mixture of heptane or hexane and ethyl acetate, and the mixture comprises over 50% by volume heptane or hexane.

22. The process of claim 1, wherein step b) comprises stirring the mixture of the compound of formula II and the base B2 for 6 h or longer.

23. The process of claim 14, wherein step b) comprises stirring the mixture of the compound of formula II and the base B2 at a temperature from 0 to 50° C.

24. The process of claim 14, wherein the compound of Formula II is a compound selected from:

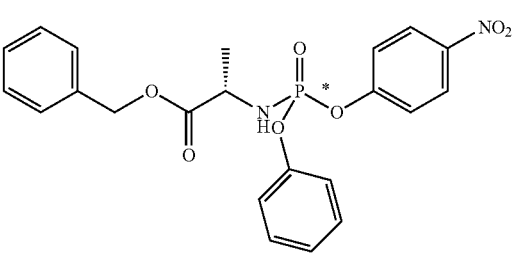

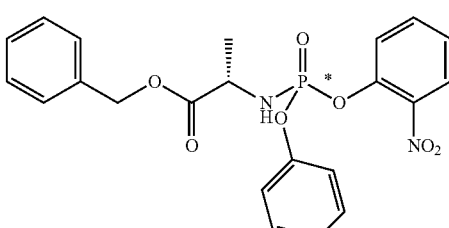

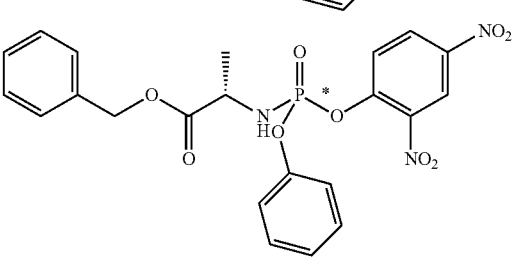

53
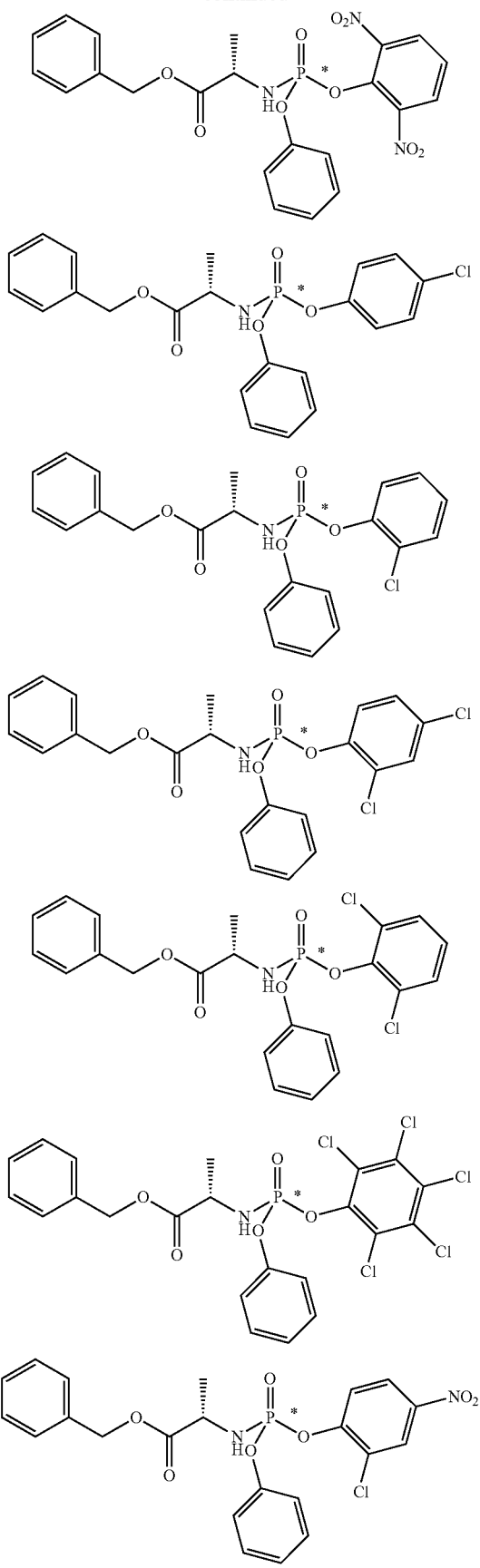
54
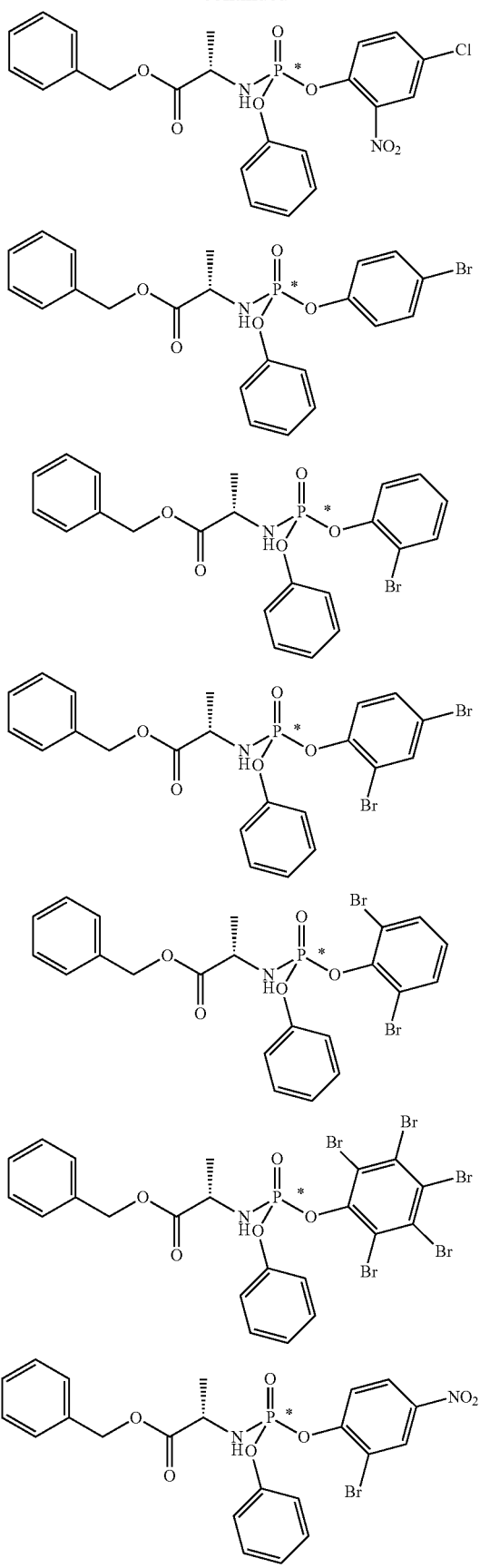

55
-continued
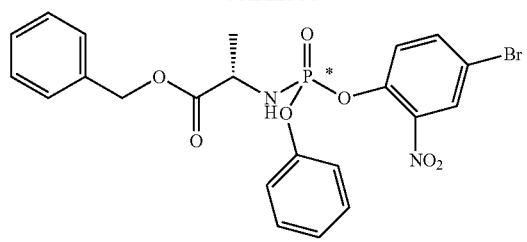
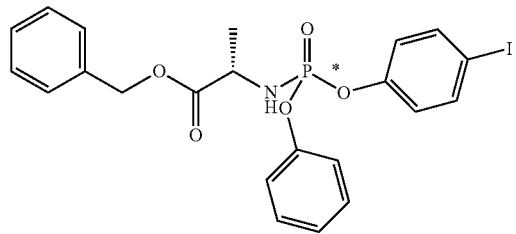
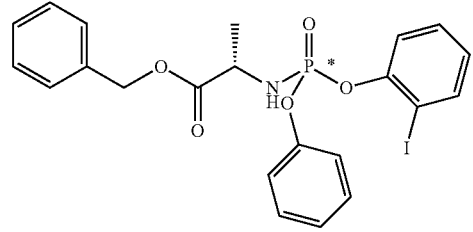
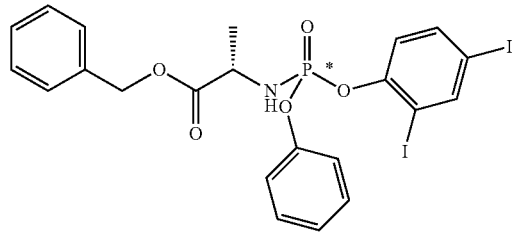
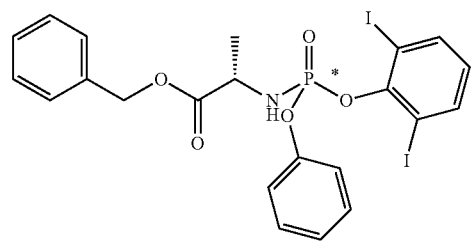
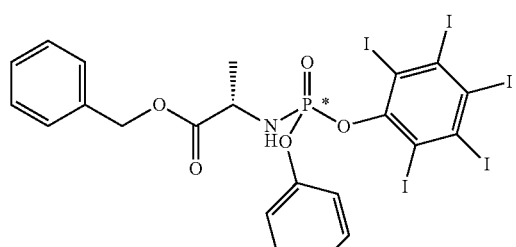
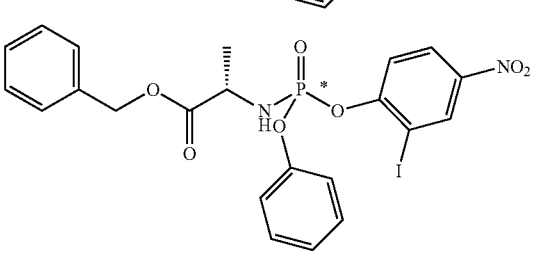
56
-continued
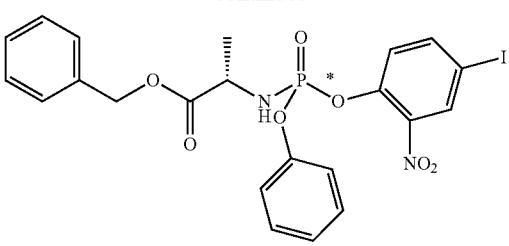
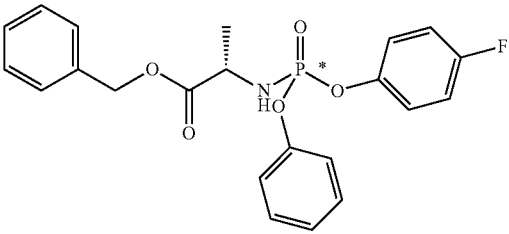
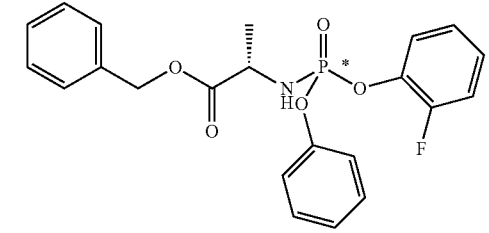
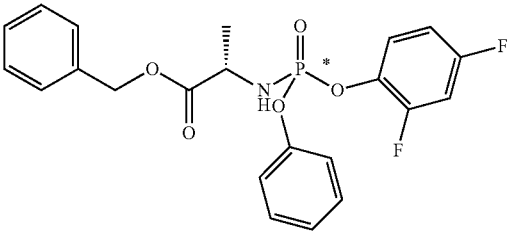
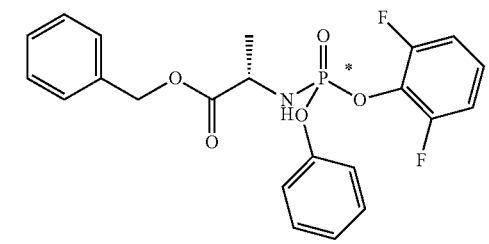
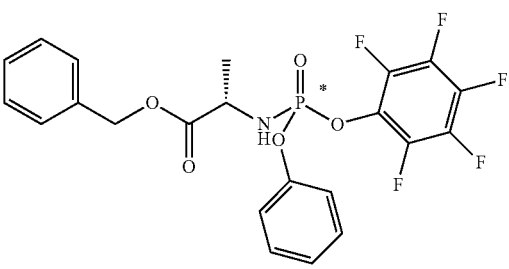
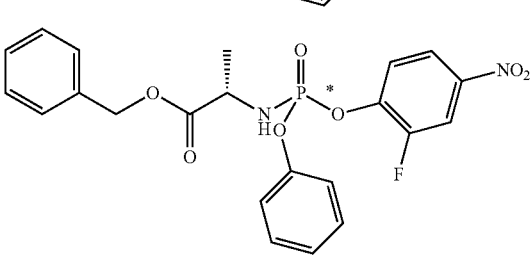

57
-continued
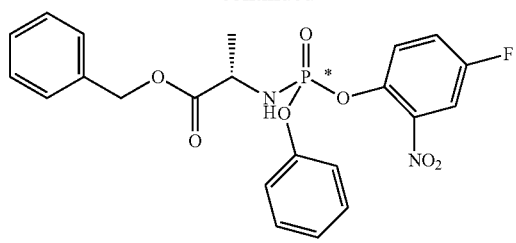
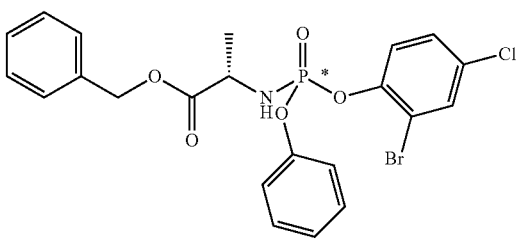
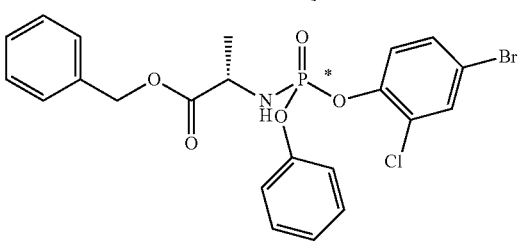
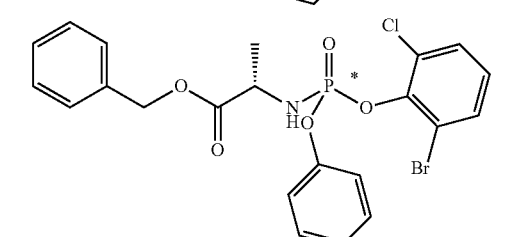
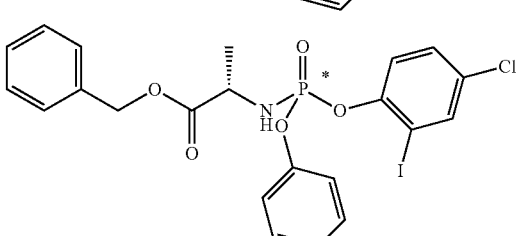
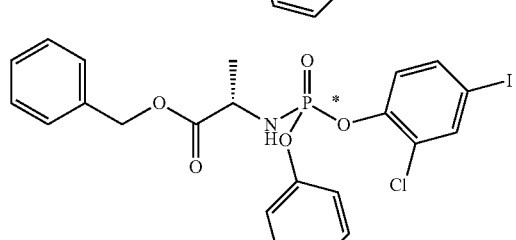
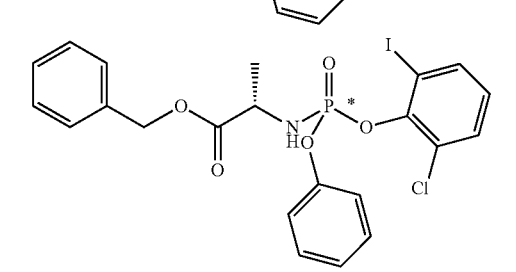
58
-continued
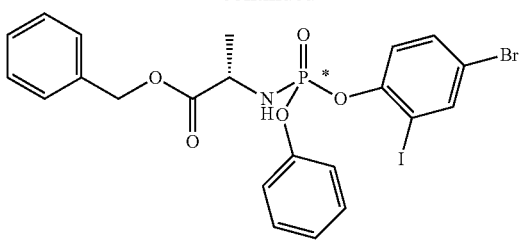
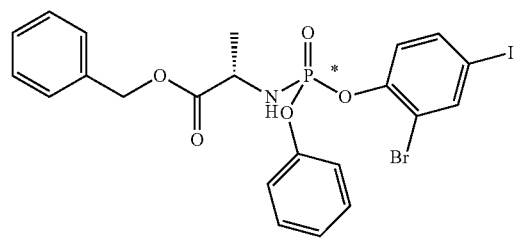
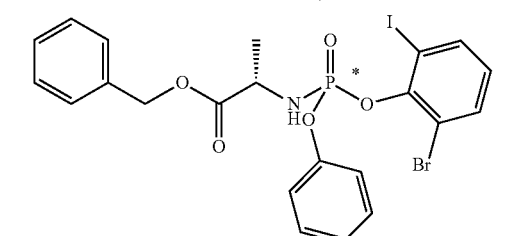
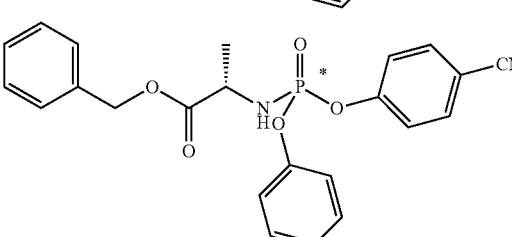
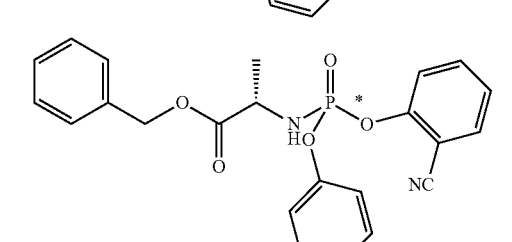
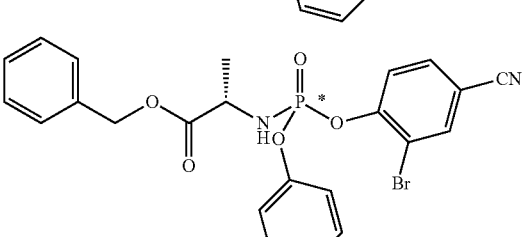
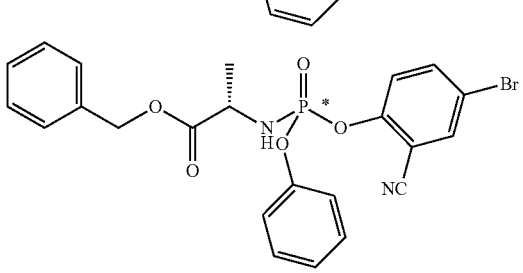

59
-continued
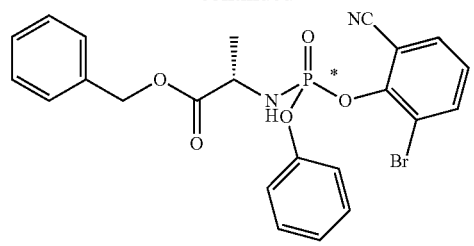
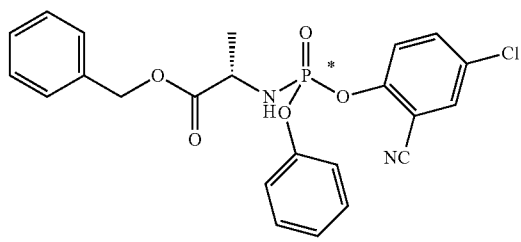
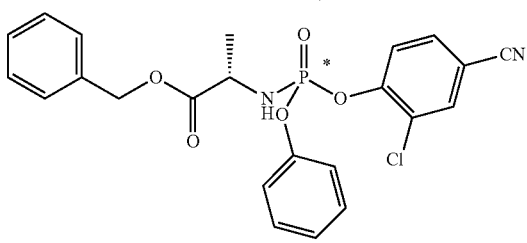
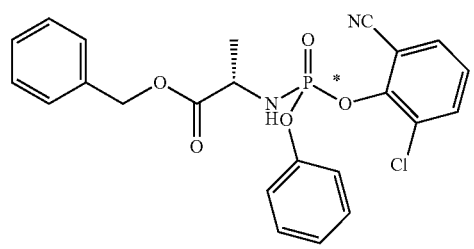
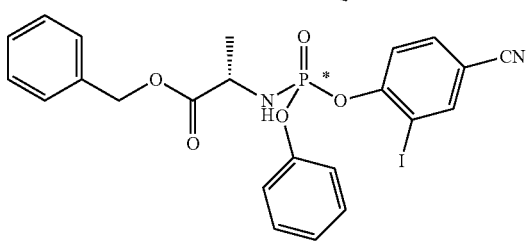
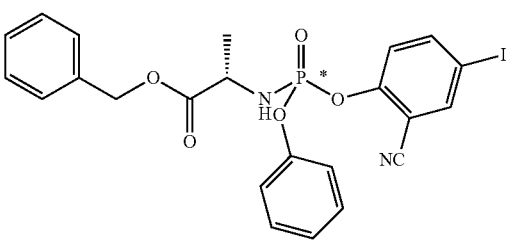
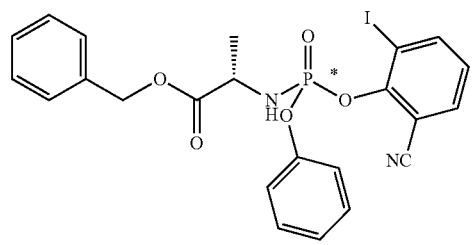
60
-continued
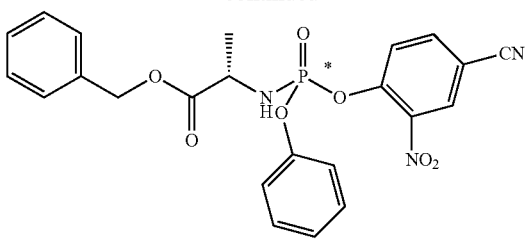
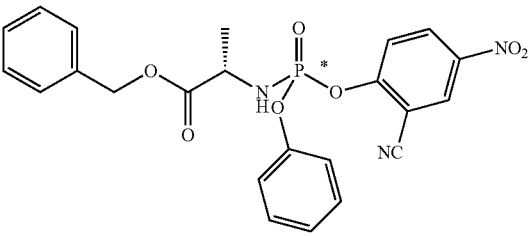
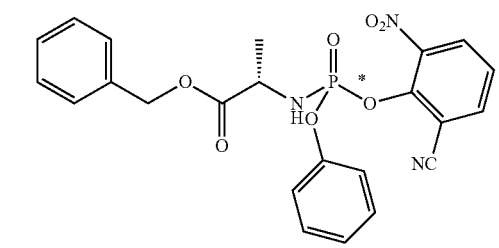
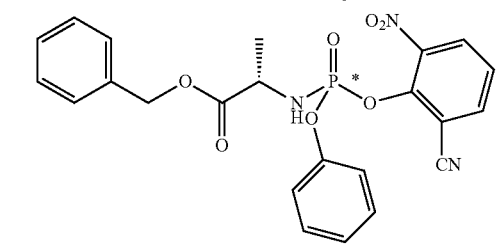
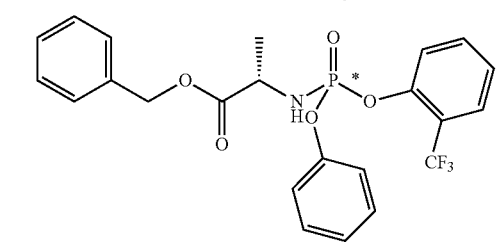
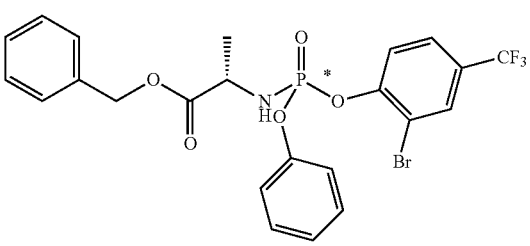
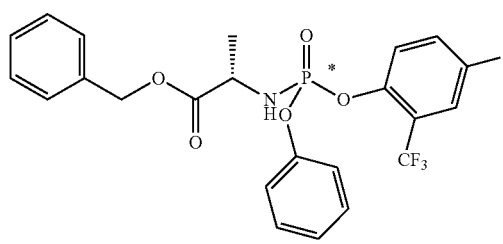

-continued
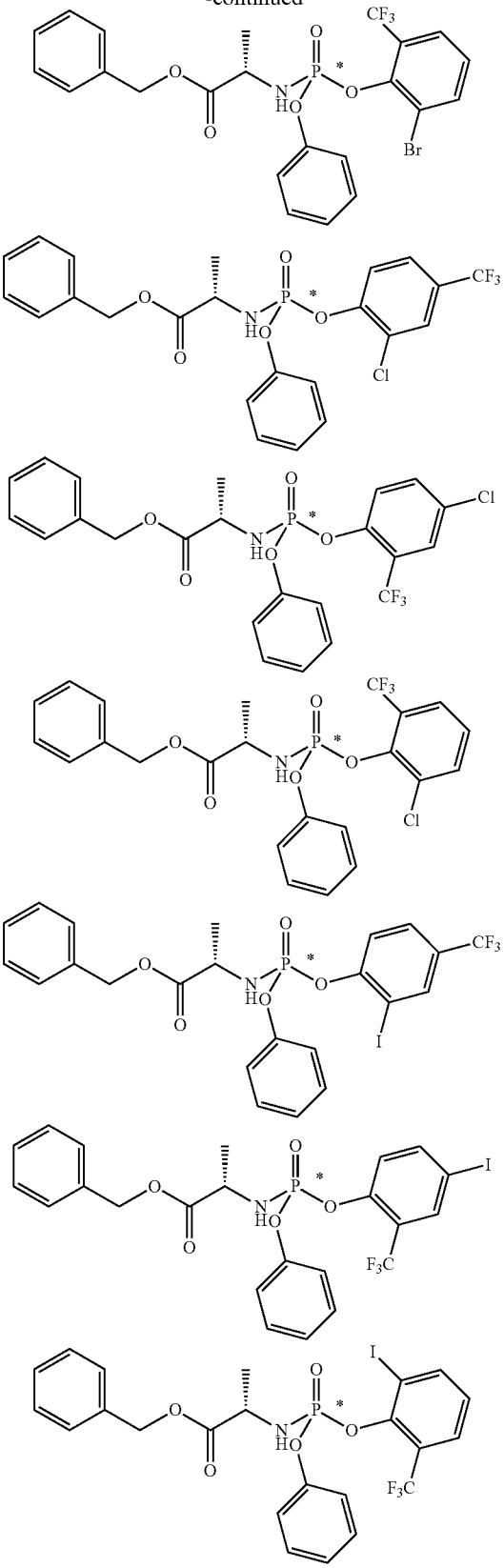
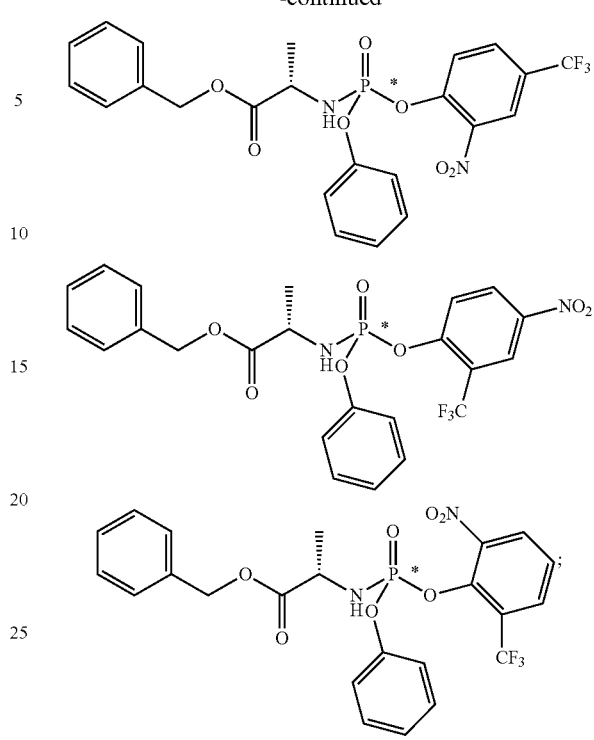
and * represents chiral center.
25. The process of claim 14, wherein the compound of formula II is:
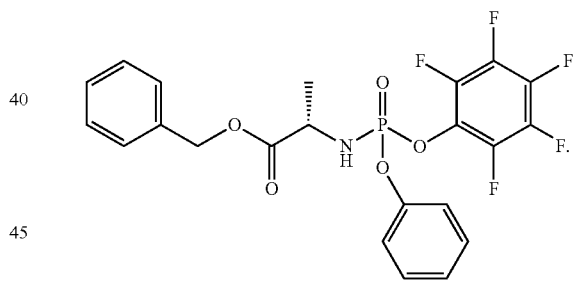
26. The process of claim 14, wherein the compound of formula II is:
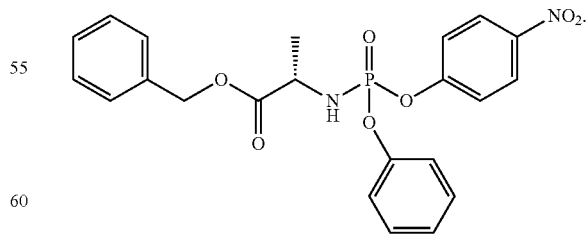
* * * * *